United States Patent
Lopez-Mejias et al.

(10) Patent No.: US 11,865,101 B2
(45) Date of Patent: Jan. 9, 2024

(54) CROMOLYN METAL COMPLEXES AS ENHANCED PHARMACEUTICAL FORMULATIONS AND METHOD OF PREPARING THE SAME

(71) Applicants: Vilmali Lopez-Mejias, San Juan, PR (US); Jeaninna P. Flores Bello, San Juan, PR (US); Israel Rodriguez Rodriguez, San Juan, PR (US); Joyce Marie Serrano Valcarcel, San Juan, PR (US)

(72) Inventors: Vilmali Lopez-Mejias, San Juan, PR (US); Jeaninna P. Flores Bello, San Juan, PR (US); Israel Rodriguez Rodriguez, San Juan, PR (US); Joyce Marie Serrano Valcarcel, San Juan, PR (US)

(73) Assignee: University of Puerto Rico, San Juan, PR (US)

(*) Notice: Subject to any disclaimer, the term of this patent is extended or adjusted under 35 U.S.C. 154(b) by 17 days.

(21) Appl. No.: 17/307,208

(22) Filed: May 4, 2021

(65) Prior Publication Data
US 2021/0338628 A1  Nov. 4, 2021

Related U.S. Application Data

(60) Provisional application No. 63/019,778, filed on May 4, 2020.

(51) Int. Cl.
*A61K 31/352* (2006.01)

(52) U.S. Cl.
CPC ........ *A61K 31/352* (2013.01); *C07B 2200/13* (2013.01)

(58) Field of Classification Search
None
See application file for complete search history.

(56) References Cited

FOREIGN PATENT DOCUMENTS

JP          06016572 A  *  1/1994

OTHER PUBLICATIONS

English Machine Translation of JP 06-016572 A (1994). Retrieved from Japanese Patent Office (Sep. 14, 2022). pp. 1-17. (Year: 1994).*
CAS Registry No. 16110-51-3. "Cromolyn". Retrieved from CAS (SciFinder) (Sep. 15, 2022). pp. 1-3. (Year: 2022).*
Rodriguez et al. "Design of Potential Pharmaceutical-Based Metal Complexes Derived from Cromolyn a Mast Cell Stabilizer". ACS Omega. Nov. 11, 2020; 5(46):29714-29721. (Year: 2020).*
Alvarez et al. "Evaluation of Metal Complexation as an Alternative to Protonation for Electrospray Ionization of Pharmaceutical Compounds". Journal of the American Society for Mass Spectrometry. 1998; 9(5):463-472. (Year: 1998).*

* cited by examiner

*Primary Examiner* — Leslie A. Royds Draper
(74) *Attorney, Agent, or Firm* — Hoglund & Pamias, PSC; Roberto J. Rios

(57) ABSTRACT

A series of pharmaceutical metal complexes (pMCs) were produced and characterized using the mast cell stabilizer, cromolyn, and bioactive metal ions ($Zn^{+2}$, $Mg^{+2}$, and $Ca^{+2}$). Three novel pMCs, Cromolyn-Zn, Cromolyn-Mg, and Cromolyn-Ca were formed through reactions under controlled temperature and pH conditions. TGA demonstrated that these metal complexes showed an enhanced thermal stability due to the strong coordination with the ligand, cromolyn. PXRD data indicates a high degree of crystallinity as well as a unique packing arrangement for each pMCs. SEM analysis showed materials with well-defined morphologies while EDS presented elemental evidence for the unique composition of each pMCs. The crystal structure for these materials was elucidated through SCXRD, and a variety of binding modes and packing motifs were found within each respective metal complex. Only 2D structures were achieved under the conditions studied. Dissolution studies show high stability and slow degradation for the metal complexes, while a higher dissolution was observed for the drug compound in PBS. Neither CS nor the pMCs dissolved significantly in FaSSGF at 37° C.

13 Claims, 32 Drawing Sheets

CROMOLYN METAL COMPLEXES AS ENHANCED PHARMACEUTICAL FORMULATIONS AND METHOD OF PREPARING THE SAME

GOVERNMENT INTEREST

This invention was made with government support under grants CHE-1626103 and HRD-1400868 awarded by the National Science Foundation (NSF) and grant GM061151 awarded by the National Institutes of Health (NIH). The Government has certain rights in this invention.

BACKGROUND OF THE INVENTION

Cromolyn sodium (CS) is a mast cell stabilizer commonly prescribed for its therapeutic role in the treatment of allergic diseases. It was originally introduced to treat allergic asthma and has quickly shown to be effective in the treatment of intestinal allergies, mastocytosis, and allergic skin conditions. Previous studies on the pharmacological actions of CS indicate that it prevents the release of mediators from mast cells, induced by specific antigens, and some studies suggest that it can also inhibit the activity of other cell types. Most recently, CS has shown activity against coronary artery disease, Alzheimer, and motor neuron diseases due to its anti-inflammatory abilities. CS can be administered via inhalation, intranasal, oral or ophthalmic routes. When delivering CS through an intranasal route it is known to cause irritation to the nasal mucosa. The transdermal route of delivery has also been investigated for CS. Here, the self-aggregation tendency of this surface-active drug (a pharmaceutically active compound with an amphiphilic nature), might make it possible to module its permeation profile.

SUMMARY OF THE INVENTION

CS is categorized as a Class III compound within the biopharmaceuticals classification system (BCS). The high solubility and low permeability presented by CS hinders its ability to be absorbed from the gastrointestinal tract (bioavailability <1%) and make it difficult to achieve a therapeutic effect when orally administered. Despite these pharmacological drawbacks, CS is still considered to be an effective drug in the treatment of allergic diseases, mainly due to being well tolerated and low in toxicity.

An approach towards the development of more robust drug delivery systems lies in the binding of ligands and bioactive metals to form metal complexes. These complexes can facilitate characterization and reduce variation in the results due to their well-defined crystalline structures, stability, and properties compared to that of polymeric drug delivery systems.

In the present invention, cromolyn (FIG. 1) is employed as a ligand, which in coordination with bioactive metals, form a series of 3D flexible metal complexes denominated as pharmaceutical metal complexes (pMCs). These crystalline materials circulate long enough to reach the target site and perform their therapeutic effect, if provided with an adequate particle size. Upon its lifetime, the metal complex, displays no adverse side-effects and enable the removal of the drug from the body through its degradation in physiological conditions. Three bioactive metals ($M^{2+}=Zn^{2+}$, $Mg^{2+}$ and $Ca^{2+}$), with lethal dose for 50% of the population ($LD_{50}$) of 1.0, 8.1 and 0.35 g/kg, were selected for their relatively low toxicity. Aside from their low toxicity, they play an important role in the regulation of inflammatory responses, which enhances the therapeutic effect of the active ingredient, CS when delivered as pMCs.

Syntheses were performed to examine the effect of $M^{2+}$/Cromolyn molar ratio, temperature, and pH on the crystallization of Cromolyn-based pMCs (FIG. 2). A number of the resulting syntheses produced crystalline materials that displayed sufficient quality for structural elucidation by single crystal X-ray diffraction (SCXRD). Additional characterization techniques were employed to assess the solid-state properties of these materials. According to an aspect of the invention, the synthesis and characterization of the resulting Cromolyn-based pMCs is discussed as well as their stability and dissolution in FaSSGF (pH=1.60) and PBS (pH=7.40) at 37° C. These Cromolyn-based pMCs can be used as novel multi-drug delivery systems to better mitigate allergic and inflammatory diseases if 3D pMCs structures containing cromolyn could be obtained and their sized controlled.

BRIEF DESCRIPTION OF THE DRAWINGS

Further features and advantages of the invention will become apparent from the following detailed description taken in conjunction with the accompanying figures showing illustrative embodiments of the invention, in which.

Figure 1:
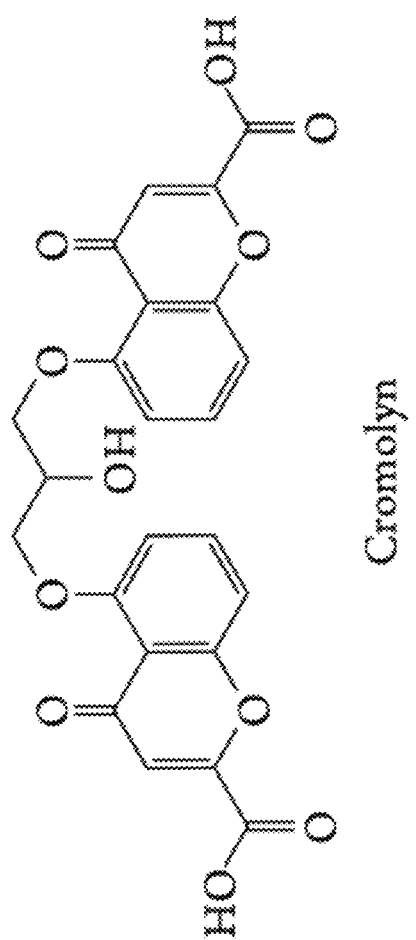
FIG. 1 shows the molecular structure of cromolyn, the ligand utilized according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Experimental Section

Materials: Calcium nitrate tetrahydrate [$Ca(NO_3)_2 \cdot 4H_2O$, 99% pure], zinc nitrate hexahydrate [$Zn(NO_3)_2 \cdot 6H_2O$, 98% pure], magnesium nitrate hexahydrate [$Mg(NO_3)_2 \cdot 6H_2O$, 99% pure], cromolyn sodium (CS, $C_{23}H_{14}O_{11}Na_2$, ≥95% pure), hydrochloric acid (HCl, 37%), ethyl alcohol [$CH_3CH_2OH$, 200 proof], and phosphate buffer saline (PBS) tablets were purchased from Sigma-Aldrich (St. Louis, MO). A stock solution of HCl (USP grade, 0.01-0.05 M) was used for pH adjustments. Nano-purified water (18.23 MOhm/cm) was utilized as obtained from a water purification system Aries Filter (Gemini) in the preparation of solvents, dissolution profiles, and synthesis. All materials were used "as received" without further purification.

General syntheses for Cromolyn-based pMCs

The syntheses of Cromolyn-based pMCs were performed by preparing CS solutions and metal salt separately in nanopure water or 50% v/v ethanol in water at room temperature. The pH of the ligand solution was adjusted with a HCl solution above the $pK_a$ of cromolyn ($pK_a$=1.90), where a partially deprotonated carboxylic acid species is expected in solution. The concentration of CS during the synthesis in both water and 1:1 water:ethanol mixtures is below 10.00 mg/mL which is noted by others as the critical self-association concentration, thus a monomeric species predominates under these conditions [CS solutions for each synthesis before the addition of the corresponding metal salt: $Zn(NO_3)_2$:CS (1.65 mg/mL, water), $Ca(NO_3)_2$:CS (2.56 mg/mL, 1:1 water:ethanol), and $Mg(NO_3)_2$:CS (2.56 mg/mL, 1:1 water:ethanol)]. Above this concentration CS forms supramolecular aggregates with liquid crystal properties. Moreover, it has been reported that aggregation of CS appeared to be pH independent, thus, even when the syntheses occur below pH 7.5, a monomeric species should still be predominant in solution. The metal salt was slowly added to the ligand solution. After mixing thoroughly, the resulting solution was heated at 70° C. until crystals appeared. Once crystals were obtained these were removed from the heat source and left undisturbed to aid the growth of the crystals. The resulting crystals were collected by vacuum filtration and air-dried. The reaction products observed in the case of Cromolyn-Zn and Cromolyn-Ca appeared as needle-like crystals whereas those obtained for Cromolyn-Mg presented a block-like morphology.

Polarized Optical Micrographs

As previously explained, the metal complexes (pMCs), Cromolyn-Zn, Cromolyn-Mg, and Cromolyn-Ca were formed through reactions under controlled temperature and pH conditions. The single crystals of the resulting pMCs were observed in a Nikon Eclipse LV100NPOL. The polarized optical micrographs displayed on FIG. 3 were processed using the NIS-Elements BR 4.30.01 software.

The conditions leading to each of the Cromolyn-based pMCs are provided in detail below.

Cromolyn-Zn—At room temperature, 0.03 mmol (0.0165 g) of solid CS was dissolved in 10.00 mL of nanopure water. The resulting ligand solution was completely transparent indicating that under these conditions a monomeric species predominates. The solution was sonicated for 10 min and the pH adjusted (pH=4.00) with 0.05 M HCl. To this solution, 0.05 mmol (0.0152 g) of $Zn(NO_3)_{2.6}H_2O$ were added to prepare a mixture with a $Zn^{2+}$/Cromolyn molar ratio of 2:1. The resulting mixture was heated at 70° C. for 7d. Clear needle-like crystals (yield <50%) were collected by vacuum filtration and air-dried.

Cromolyn-Mg—At room temperature, 0.05 mmol (0.0256 g) of solid CS was dissolved in 10.00 mL of 50% v/v ethanol in water. The resulting ligand solution was completely transparent indicating that under these conditions a monomeric species predominates. The solution was sonicated for 10 min and the pH adjusted (pH=4.00) with 0.02 M HCl. To this solution, 0.05 mmol (0.0127 g) of Mg $(NO_3)_2 \cdot 6H_2O$ was added to prepare a mixture with a $Mg^{2+}$/Cromolyn molar ratio 1:1. The resulting mixture was heated at 70° C. for 7d. Clear block-like crystals (yield <50%) were collected by vacuum filtration and air-dried.

Cromolyn-Ca—At room temperature, 0.05 mmol (0.0256 g) of solid CS was dissolved in 10.00 mL of 50% v/v ethanol in water. The resulting ligand solution was completely transparent indicating that under these conditions a monomeric species predominates. The solution was sonicated for 10 min and the pH adjusted (pH=4.00) with 0.02 M HCl. To this solution, 0.1 mmol (0.0236 g) of $Ca(NO_3)_2 \cdot 6H_2O$ was added to prepare a mixture with a $Ca^{2+}$/Cromolyn molar ratio 2:1. The resulting mixture was heated at 70° C. for 7d. Clear needle-like crystals (yield <50%) were collected by vacuum filtration and air-dried.

Raman microscopy—Raman spectra were recorded in a Thermo Scientific DXR Raman microscope, equipped with a 532 nm laser, 400 lines/nm grating, and 50 μm slit. The spectra were collected at room temperature over the range of 2,000 and 200 $cm^{-1}$ by averaging 32 scans with exposures of 5 sec. This data was collected and analyzed int the OMNIC for Dispersive Raman software version 9.2.0.

Scanning electron microscopy-energy dispersive spectroscopy (SEM-EDS). Micrographs and X-ray microanalysis were recorded with a JEOL JSM-6480LV scanning electron microscope with an Evenhart Thomley secondary electron imagining (SEI) detector and an energy dispersive X-ray analysis (EDAX) Genesis 2000 detector. Images were taken with an acceleration voltage of 20 kV, an electron beam of 11 mm width, with a spot size value of 36, SEI signal and high vacuum mode.

Powder X-ray diffraction (PXRD)—Powder diffractograms were collected in transmission mode using a Rigaku XtaLAB SuperNova X-ray diffractometer with a microfocus Cu-Kα radiation (λ=1.5417 Å, 50 kV, 1 mA) source and equipped with a HyPix3000 X-ray detector. Dry crystals of the pMCs were grinded to a fine powder before being transferred into a MiTGen loop with paratone oil for PXRD analysis. Powder diffractograms were collected over an angular 2θ range between 5-50° with a step of 0.01° using a Gandolfi move experiment for powders. An Oxford Cryosystems Cryostream 800 cooler was used to collect the powder data at 300 K. PXRD data was analyzed using the CrystAllisPRO software v. 1.171.3920a.

Single crystal X-ray diffraction (SCXRD)—A Nikon Eclipse Microscope LV100NPOL, equipped with a Nikon DS-Fi2 camera was used to observe crystals and assess their quality. Optical micrographs were recorded and process within the NIS Elements BR software version 4.30.01. Single crystals were removed from storage vials and placed on a microscope slide inside a drop of paratone oil. Later, MiTeGen micro loops were used to mount the best single crystals for structure elucidation. A Rigaku XtaLAB SuperNova single micro-focus Cu-Kα radiation (λ=1.5417 Å, 50 kV, 1 mA) source equipped with a HyPix3000 X-ray detector in transmission mode was used to collect the SCXRD data. An Oxford Cryosystems Cryostream 800 cooler controlled the temperature at 100 K. Data was collected and initially refined within the CrystAllis$^{PRO}$ software v. 1.171.39.43c. All crystal structures were solved by direct methods. Final refinement of each structure was performed using full-matrix least squares on $F^2$ within the Olex2 (v1.2-ac3) software. Non-hydrogen atoms were anisotropically refined.

Thermogravimetric analysis (TGA)—TGA of CS and pMCs were recorded using a Q500 from TA Instruments Inc. About 2 mg of material was thermally treated from 10 to 700° C. at 5° C./min under a $N_2$ gas purge. TA Universal Analysis software version 4.3A was used to analyze the TGA data.

Dissolution profiles—Dissolution profiles were recorded for CS, Cromolyn-Zn, Cromolyn-Mg, and Cromolyn-Ca and quantified by measuring absorbance at 237 nm against a reagent blank containing the buffered media. Dissolution tests were performed in a PBS buffer (pH=7.40) and FaSSGF (pH=1.60) at 37° C. under constant stirring (150 rpm). Absorbance measurements were performed on an Agilent Technologies Cary Series UV-Vis Spectrophotometer, Cary 100 UV-Vis model; using the UV Cary Scan software version v.20.0.470.

RESULTS AND DISCUSSION

Figure 2:
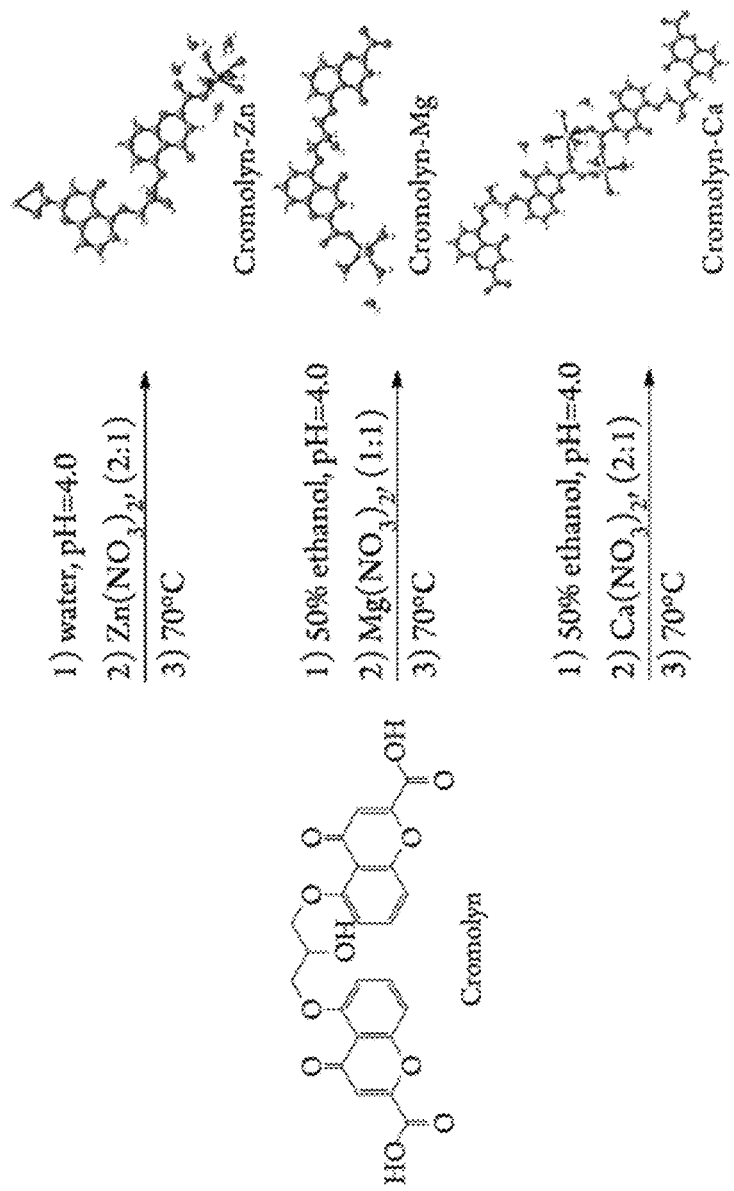
FIG. 2 shows a schematic diagram of the conditions leading to three crystalline phases when cromolyn is coordinated with three bioactive metals ($Zn^{2+}$, $Mg^{2+}$ and $Ca^{2+}$) to form pharmaceutical metal complexes (pMCs). The variables explored were: $M^{2+}$/Cromolyn molar ratio, reaction temperature, and pH.
Figure 3:
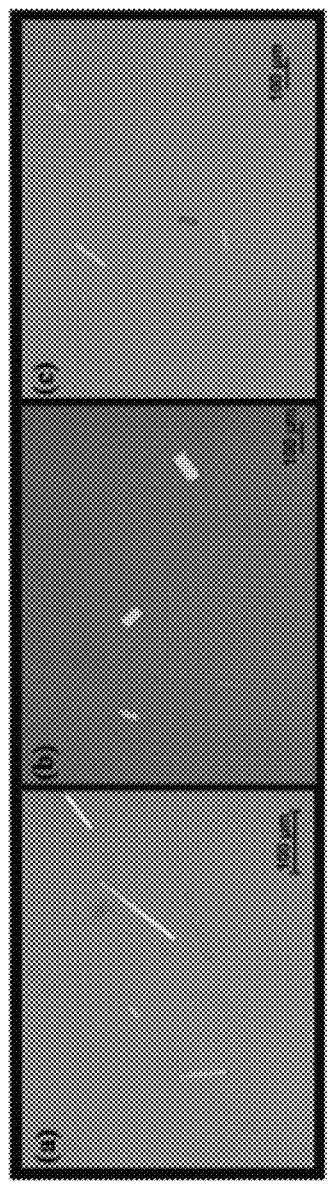
FIG. 3 shows polarized optical micrographs of three pharmaceutical metal complexes (pMCs) depicting single crystals of (a) Cromolyn-Zn, (b) Cromolyn-Mg, and (c) Cromolyn-Ca for the Cromolyn-based metal complexes.

Synthesis of cromolyn (FIG. 1) with three bioactive metal ions were performed considering the following parameters: $M^{2+}$/cromolyn molar ratio (1:1, 1:2, 1:3, 2:1, 2:3, 3:1), temperature (25, 45, 65, 70, 80, 85, and 120° C.), and pH (4.00-5.00) of the reaction. The conditions that lead to the production of the best single crystals for Cromolyn-Zn, Cromolyn-Mg, and Cromolyn-Ca are shown in FIG. 2. The pH of the ligand solution was adjusted above the $pK_a$ of cromolyn ($pK_a$=1.90) to achieve a partially deprotonated species in solution which is thought to speed the reaction. The pH of the final solution (Cromolyn+$M^{2+}$) should also be below the pH leading to the formation of a metal oxide. The initial pH of the ligand solution before the addition of the metal salts was ~6.00. A dilute solution of HCl (0.01-0.05 M) was employed to adjust the pH to 4.00. At this pH an increased in the rate of the crystallization was observed. This pH also seems to facilitate the formation of single crystal quality crystals of the Cromolyn-based pMCs. Optical micrographs for the single crystals obtained for Cromolyn-Zn, Cromolyn-Ca, and Cromolyn-Mg are shown in FIG. 3. Other conditions lead to significantly smaller crystals and/or microcrystalline powders.

Figure 4:
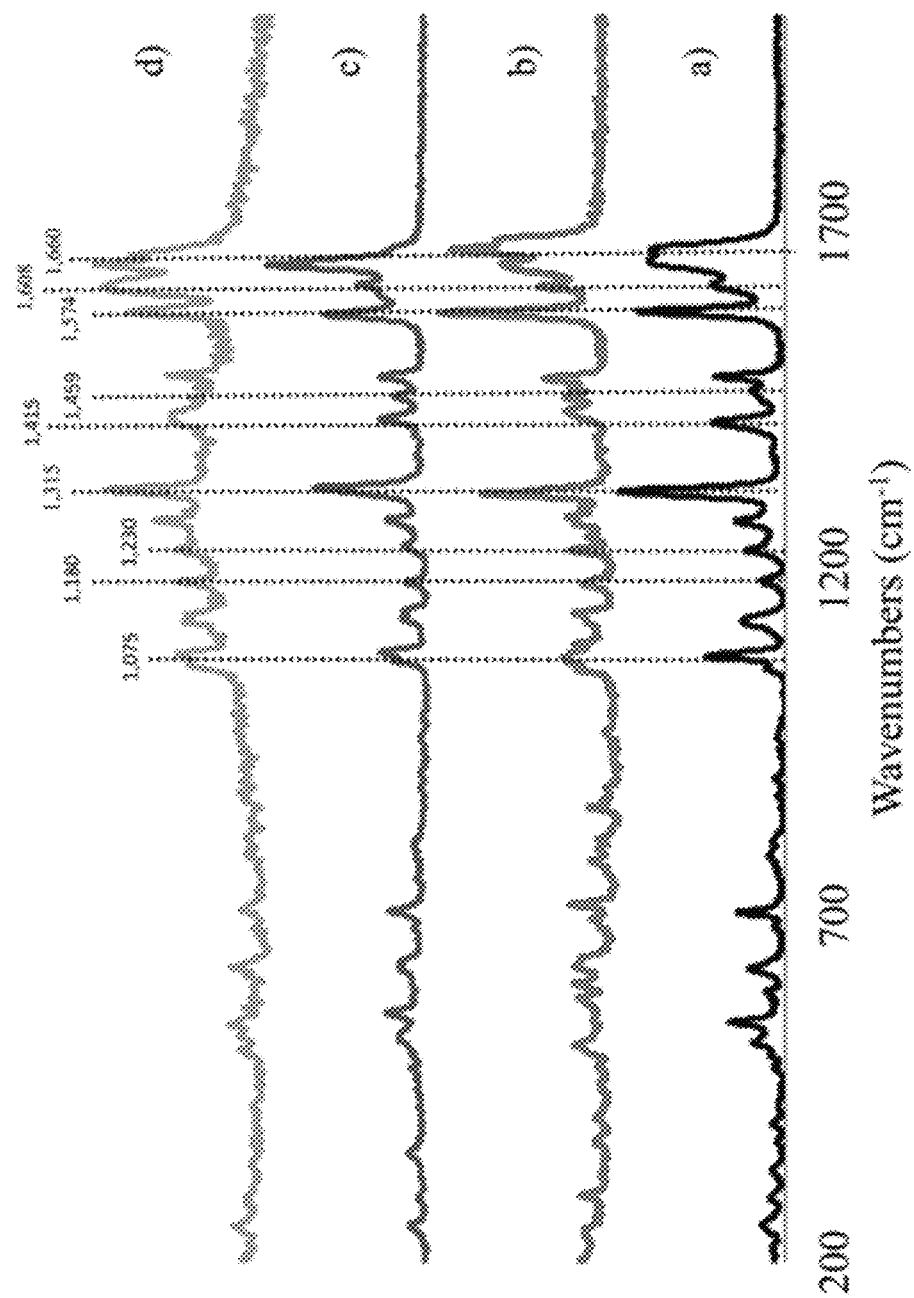
FIG. 4 shows Raman spectra overlay of (a) "as received" CS, and Cromolyn-based pMCs; (b) Cromolyn-Zn, (c) Cromolyn-Mg, and (d) Cromolyn-Ca.

Raman spectroscopy results—Raman spectroscopy was used to analyze the crystals obtained from the reaction between cromolyn with $Zn^{2+}$, $Mg^{2+}$, and $Ca^{2+}$. The Raman spectra were collected in the range of 2,000 to 200 $cm^{-1}$ and are shown in FIG. 4. The region between 1,700 and 1,200 $cm^{-1}$ is associated with vibrational modes of the carboxylate moiety. The carboxylate groups have been shown to change orientation in this region due to the coordination or entrapment of water molecules in the different structures. An expansion in the unit cell is usually followed by changes in the crystalline structure and these were confirmed through the observation of peak shifts in the different Raman spectra.

The vibrational mode associated with the asymmetric stretching of ketones is found near 1,660 $cm^{-1}$, with a strong C=O frequency absorption. Additional functional groups covalently attached to the ketone, such as the ether moiety and carboxylate display meaningful peaks in the Raman spectra. The asymmetric stretching vibrational modes of carboxylic acid moiety occurs near 1,574 $cm^{-1}$ and this is found in the Raman spectra of CS and all the metal complexes that were analyzed. The $CH_2$ next to the carbonyl presents a strong band as a result of $CH_2$ deformation at 1,415 $cm^{-1}$, such a peak is observed on the Raman spectra obtained for CS. Changes observed in the Raman spectra of the metal complexes included a shift in this peak occurring at around 1,430 $cm^{-1}$ in Cromolyn-Zn, Cromolyn-Mg, and Cromolyn-Ca. Additionally, an asymmetric stretching (C—C—C) vibration in the $CH_2$—CO—$CH_2$ functional group present in this compound produces a medium intensity band between 1,230 and 1,315 cm$^{-1}$. Sharp bands close to 1,608, 1,459, and 1,479 cm$^{-1}$ are representative of u(C═C) aromatic ring chain asymmetric stretching vibrations which are bonded to the ether moiety in CS. The vibrational mode of the ether moiety can be associated to the region between 1,180-1,075 cm$^{-1}$. This can be observed as weak intensity peaks in the Raman spectra of all the metal complexes and CS. The bands located at lower wavenumbers (<1,000 cm$^{-1}$) match the vibrational modes characteristics of the CH$_2$, C—C, and C—OH, which are functional groups present in the Raman spectra of CS.

Figure 5:
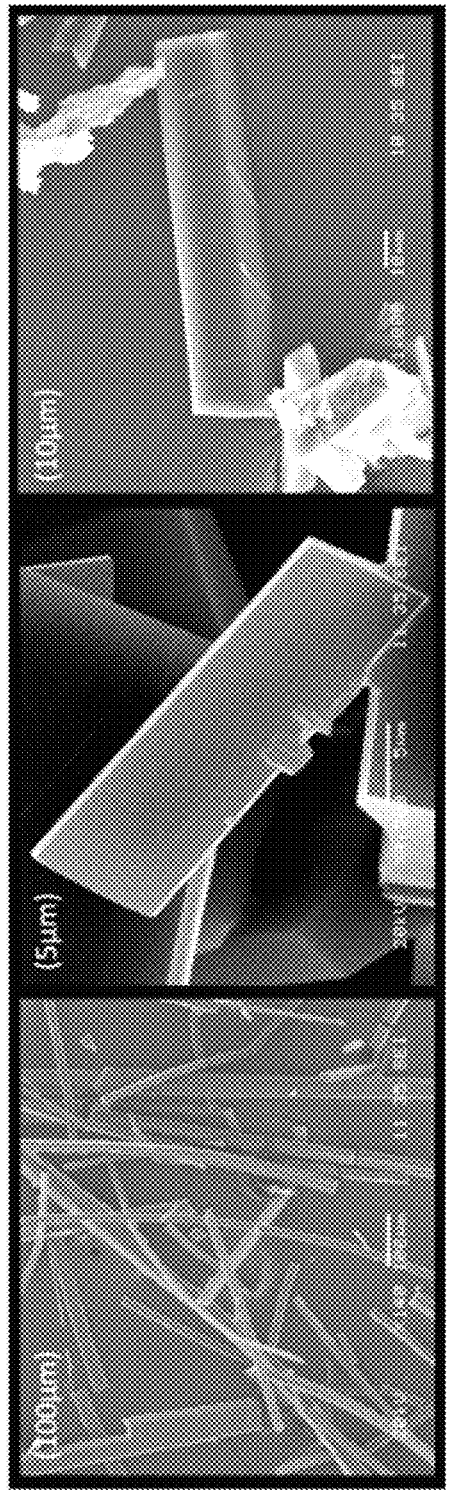
FIG. 5 shows scanning electron micrographs for cromolyn in coordination with the respective bioactive metals forming Cromolyn-based pMCs; Cromolyn-Zn (left), Cromolyn-Mg (middle), and Cromolyn-Ca (right).

Scanning Electron Microscope Coupled with Energy Dispersive Spectroscopy (SEM-EDS) results—The representative SEM micrographs collected for the isolated crystalline phases display crystals with well-defined morphologies and a resulting diameter ranging between 10-50 μm (FIG. 5). The EDS spectra for these materials exhibit the characteristic signals representative of the corresponding metal and other elements which are present in the molecular structure of CS including both carbon and oxygen atoms.

Figure 6:
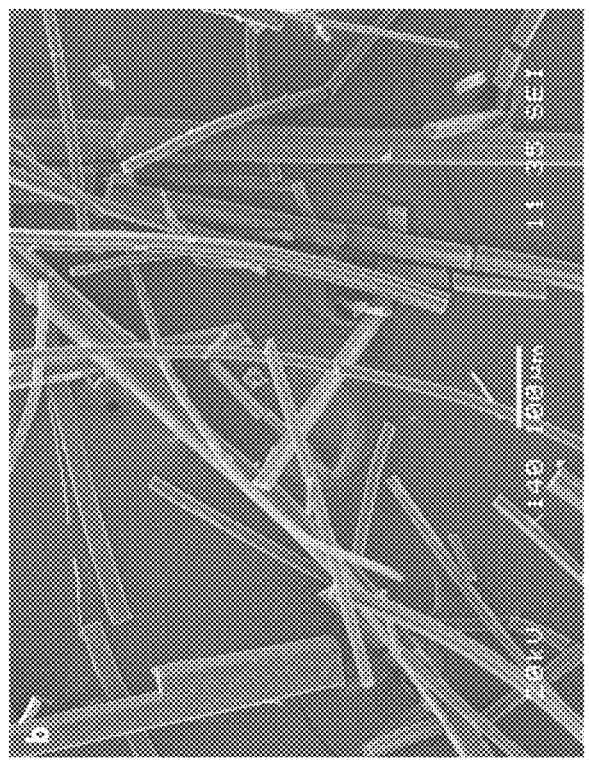
FIG. 6 shows scanning electron micrographs of (a) Cromolyn-Zn single crystal at a 180× magnification, and (b) crystals of Cromolyn-Zn at a 140× magnification.
Figure 6:
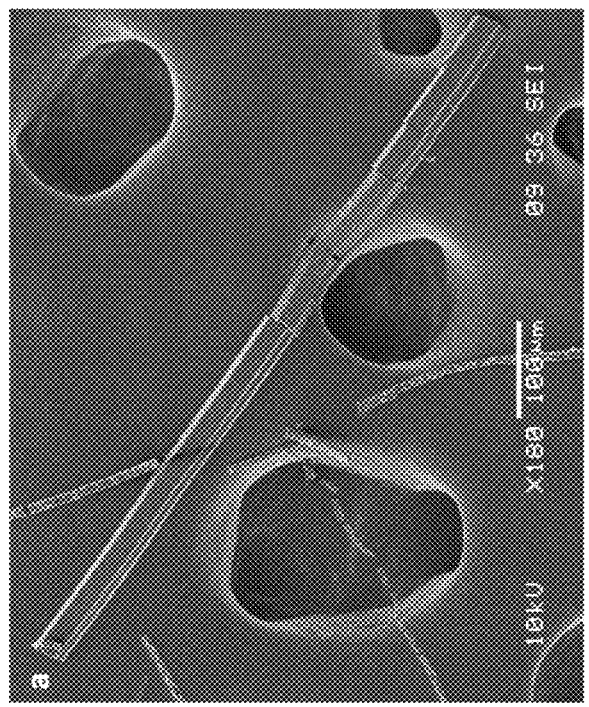
Figure 7:
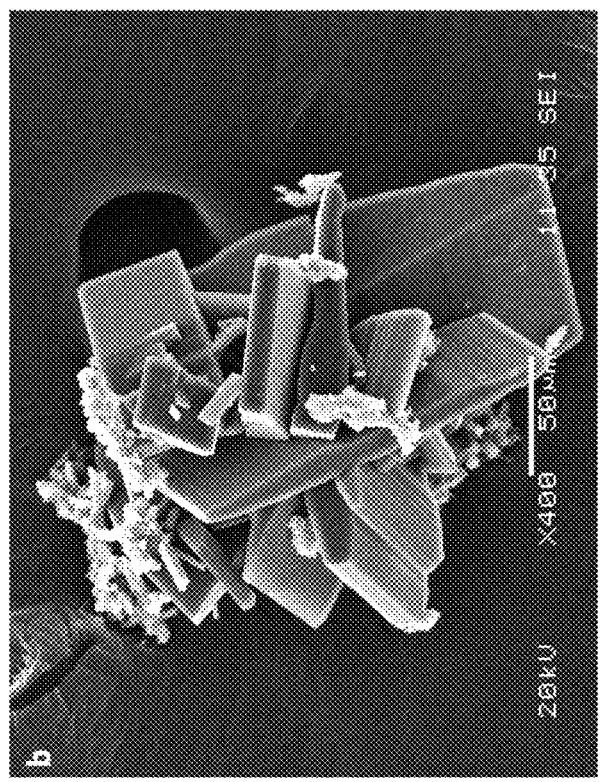
FIG. 7 shows scanning electron micrographs of (a) Cromolyn-Mg single crystal at a 4,500× magnification, and (b) crystals of Cromolyn-Mg at a 400× magnification.
Figure 7:
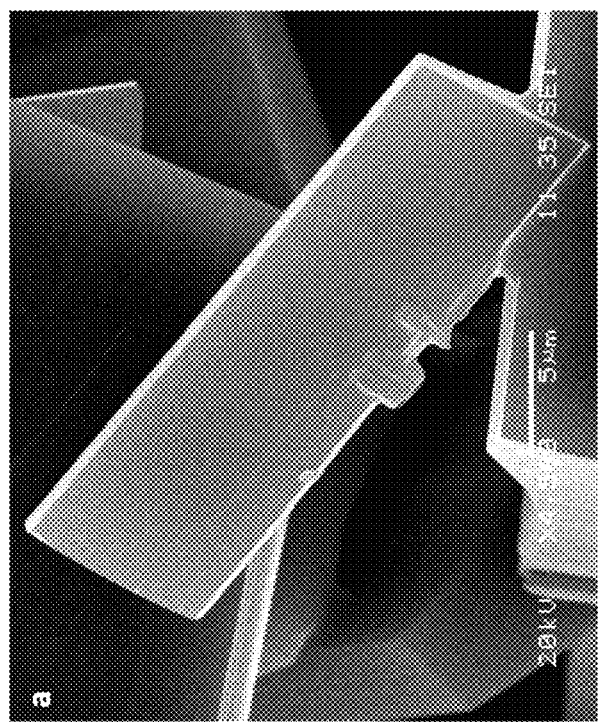
Figure 8:
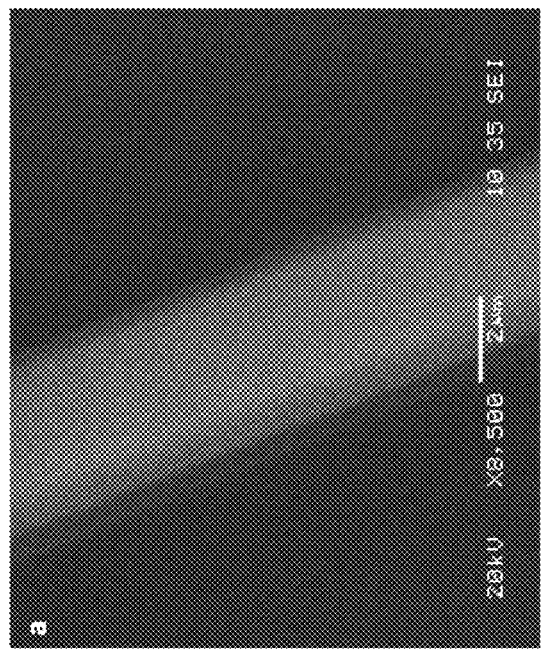
FIG. 8 shows scanning electron micrographs of (a) Cromolyn-Ca single crystal at a 8,500× magnification, and (b) crystals of Cromolyn-Ca at a 500× magnification.
Figure 8:
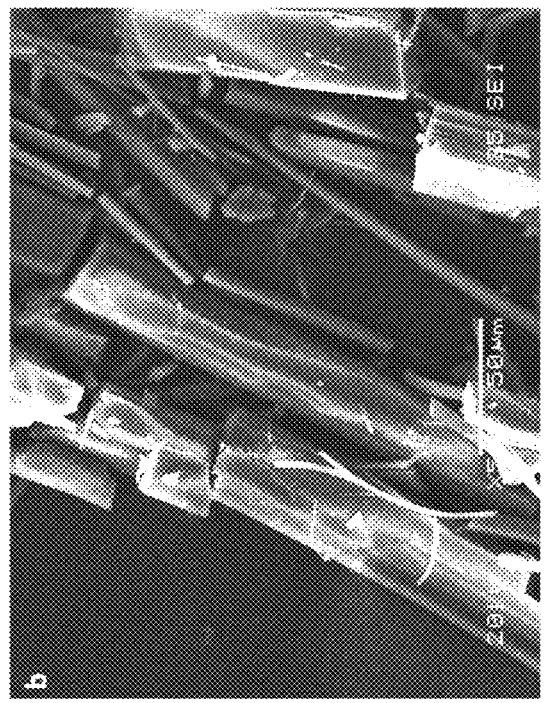
Figure 9:
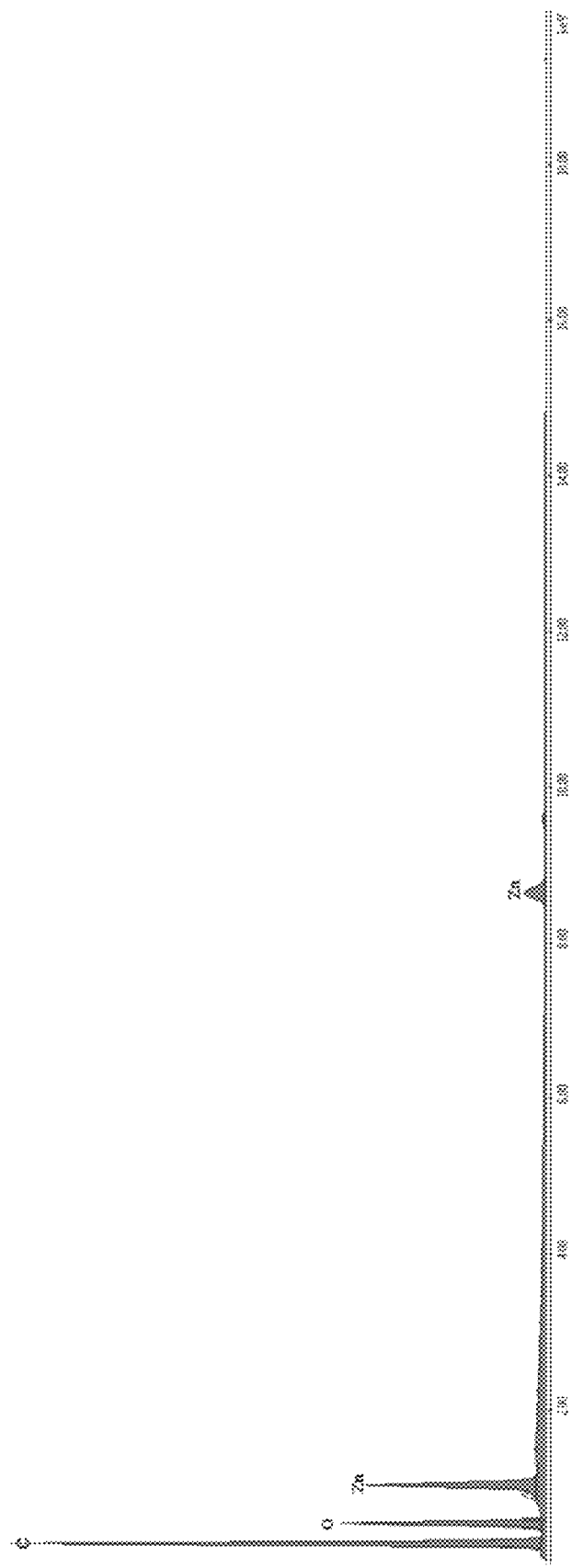
FIG. 9 shows energy dispersive spectra of Cromolyn-Zn displaying the presence of atoms (carbon and oxygen) present in cromolyn and the metal (zinc).
Figure 10:
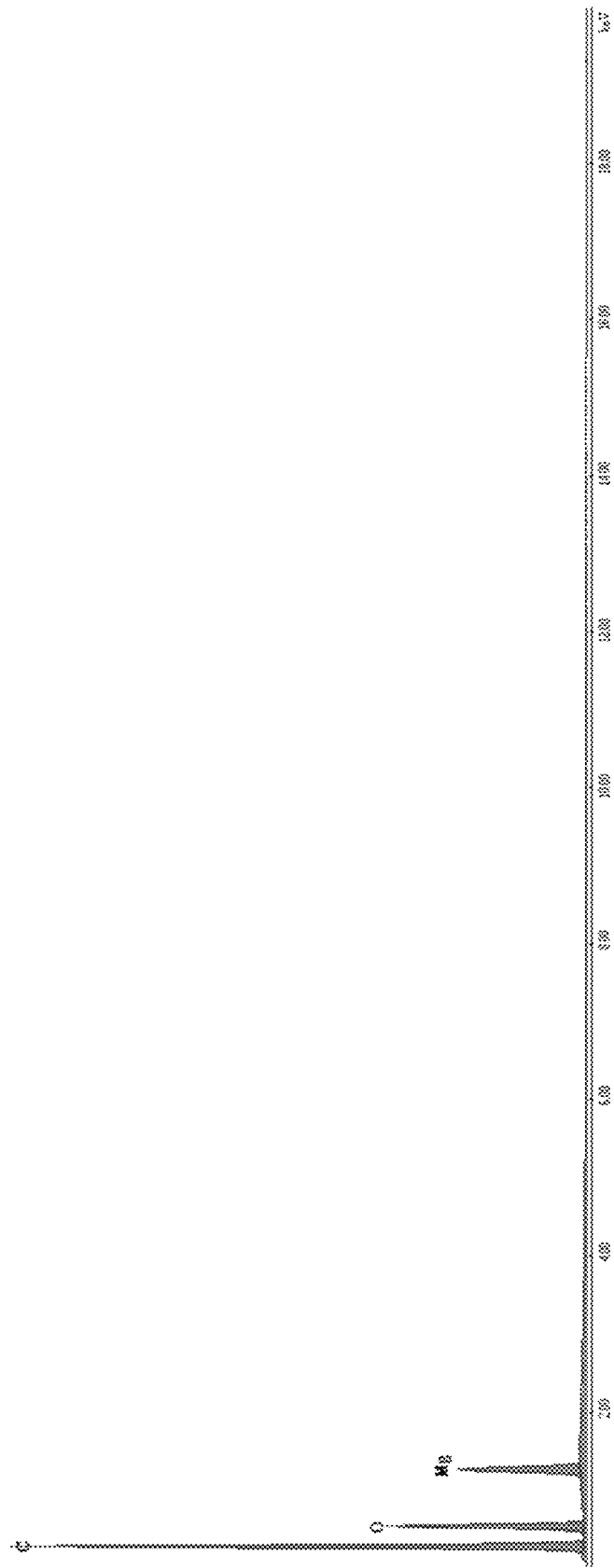
FIG. 10 shows energy dispersive spectra of Cromolyn-Mg displaying the presence of atoms (carbon and oxygen) present in cromolyn and the metal (magnesium).
Figure 11:
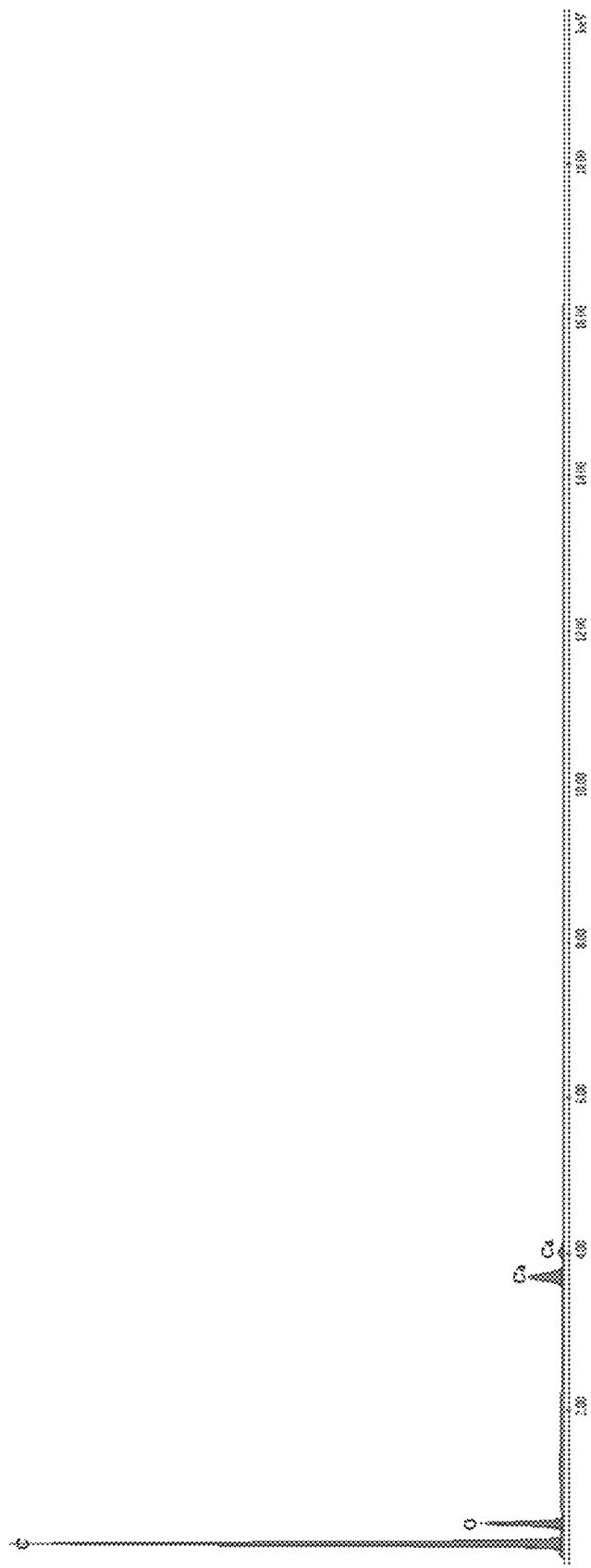
FIG. 11 shows energy dispersive spectra of Cromolyn-Ca displaying the presence of atoms (carbon and oxygen) present in cromolyn and the metal (calcium).

FIGS. 6-8 represent scanning electron micrographs of Cromolyn-Zn, Cromolyn-Mg, and Cromolyn-Ca showing clusters and single crystals and FIGS. 9-11 depict the energy dispersive spectra for the synthesized Cromolyn-Zn, Cromolyn-Mg, and Cromolyn-Ca.

Figure 12:
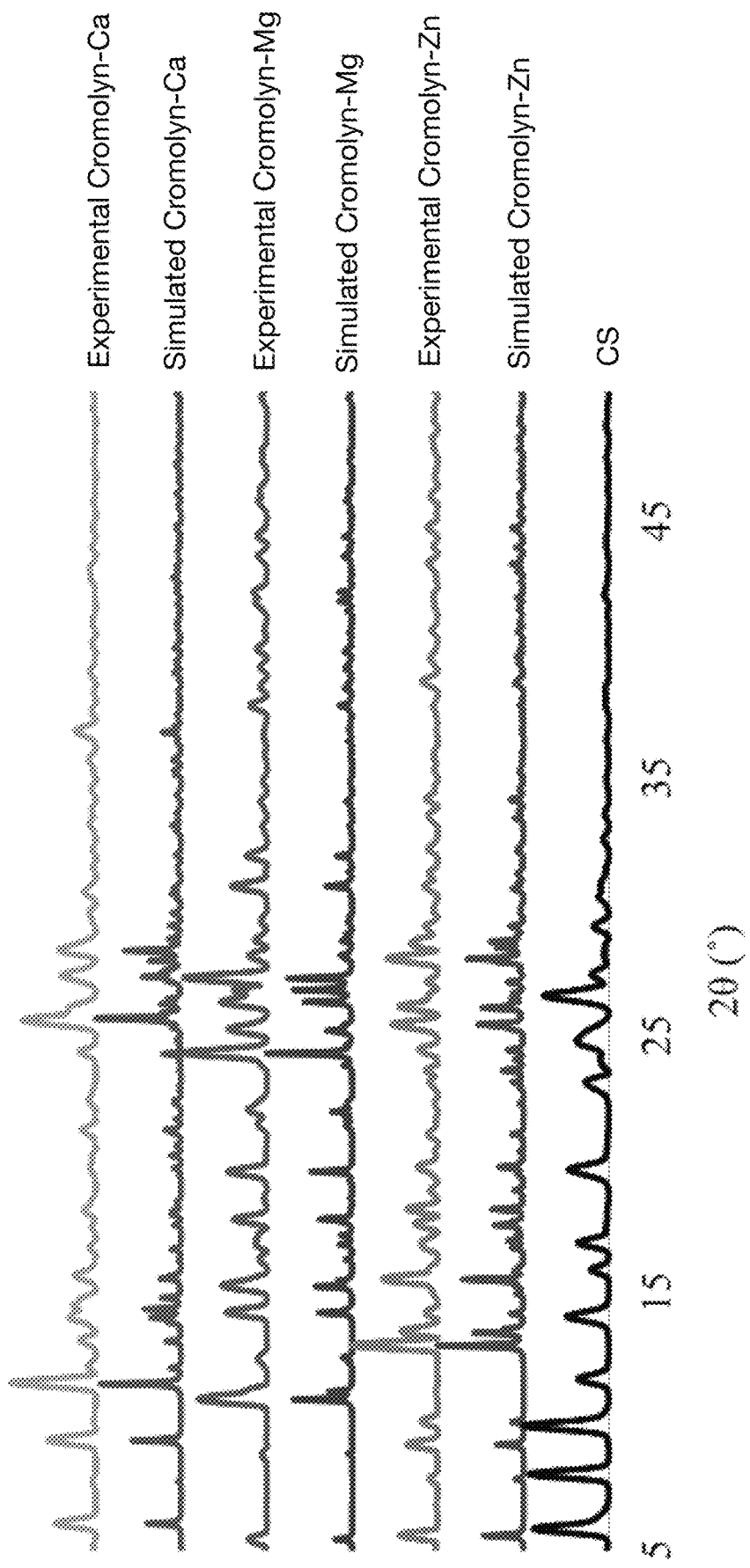
FIG. 12 shows simulated and experimental powder X-ray diffractograms of CS, Cromolyn-Zn, Cromolyn-Mg, and Cromolyn-Ca carried out at 100 K.
Figure 13:
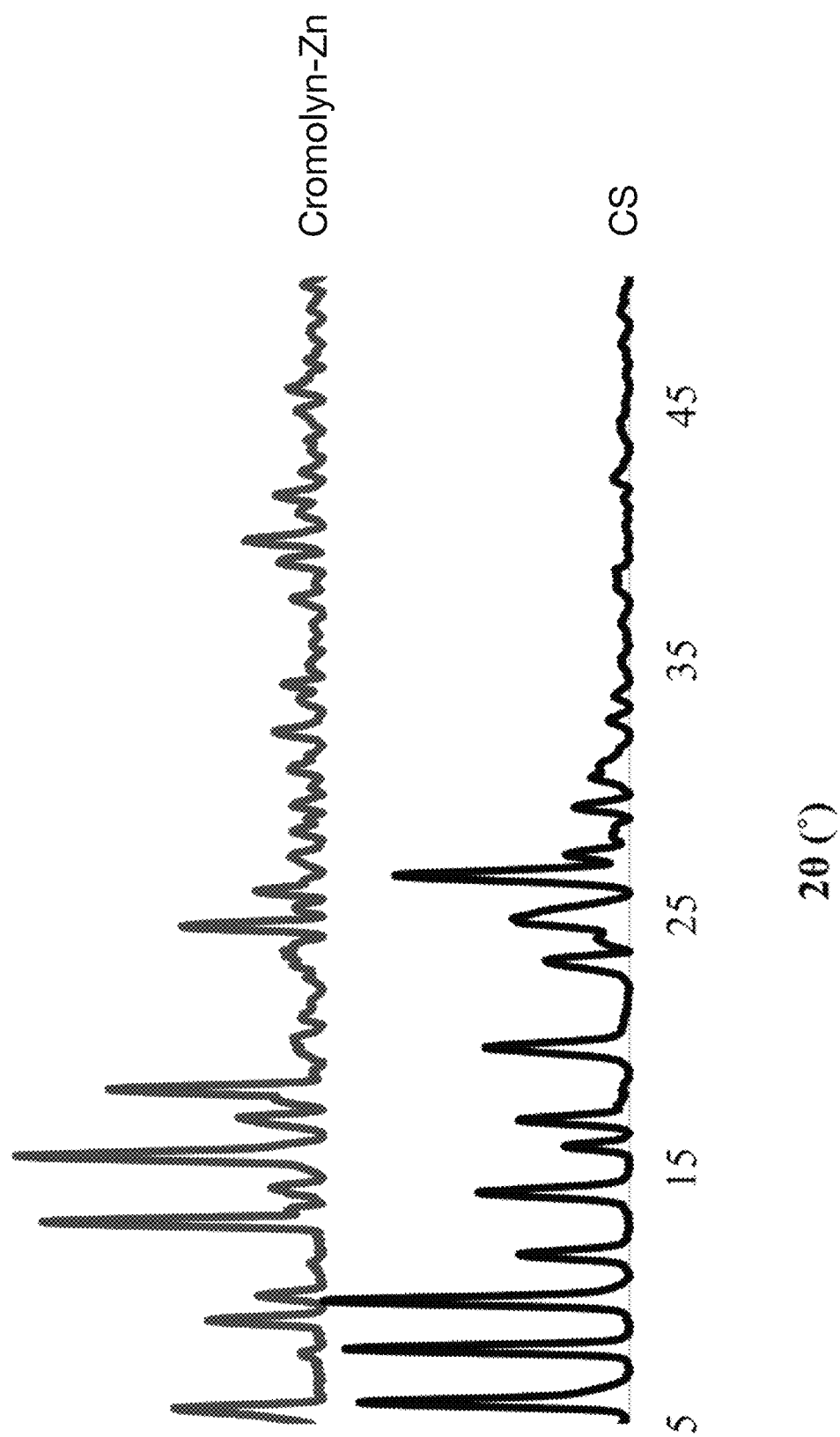
FIG. 13 illustrate the overlay of the experimental powder X-ray diffraction pattern of "as received" CS compared to synthesized Cromolyn-Zn.
Figure 14:
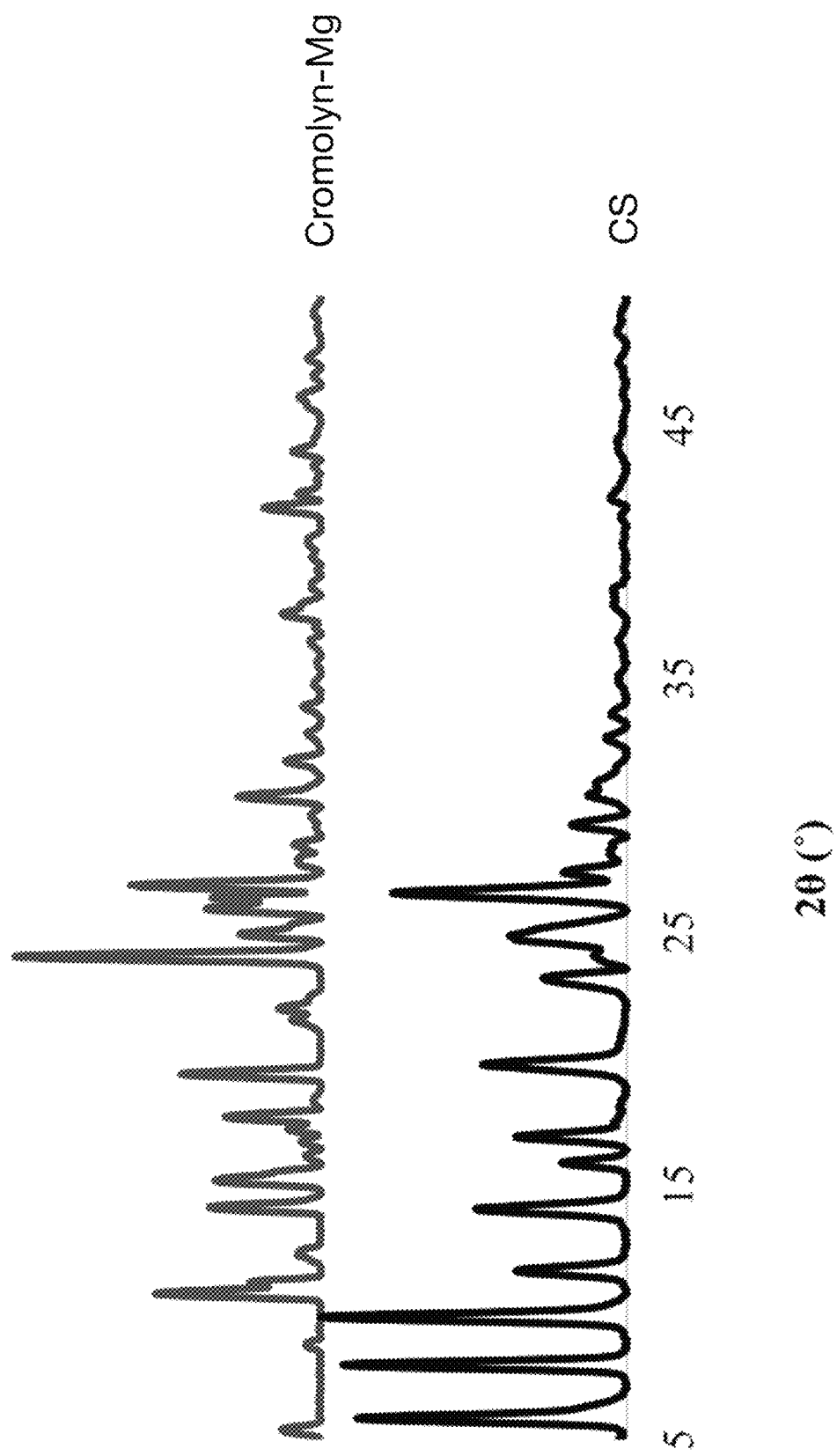
FIG. 14 illustrate the overlay of the experimental powder X-ray diffraction pattern of "as received" CS compared to synthesized Cromolyn-Mg.
Figure 15:
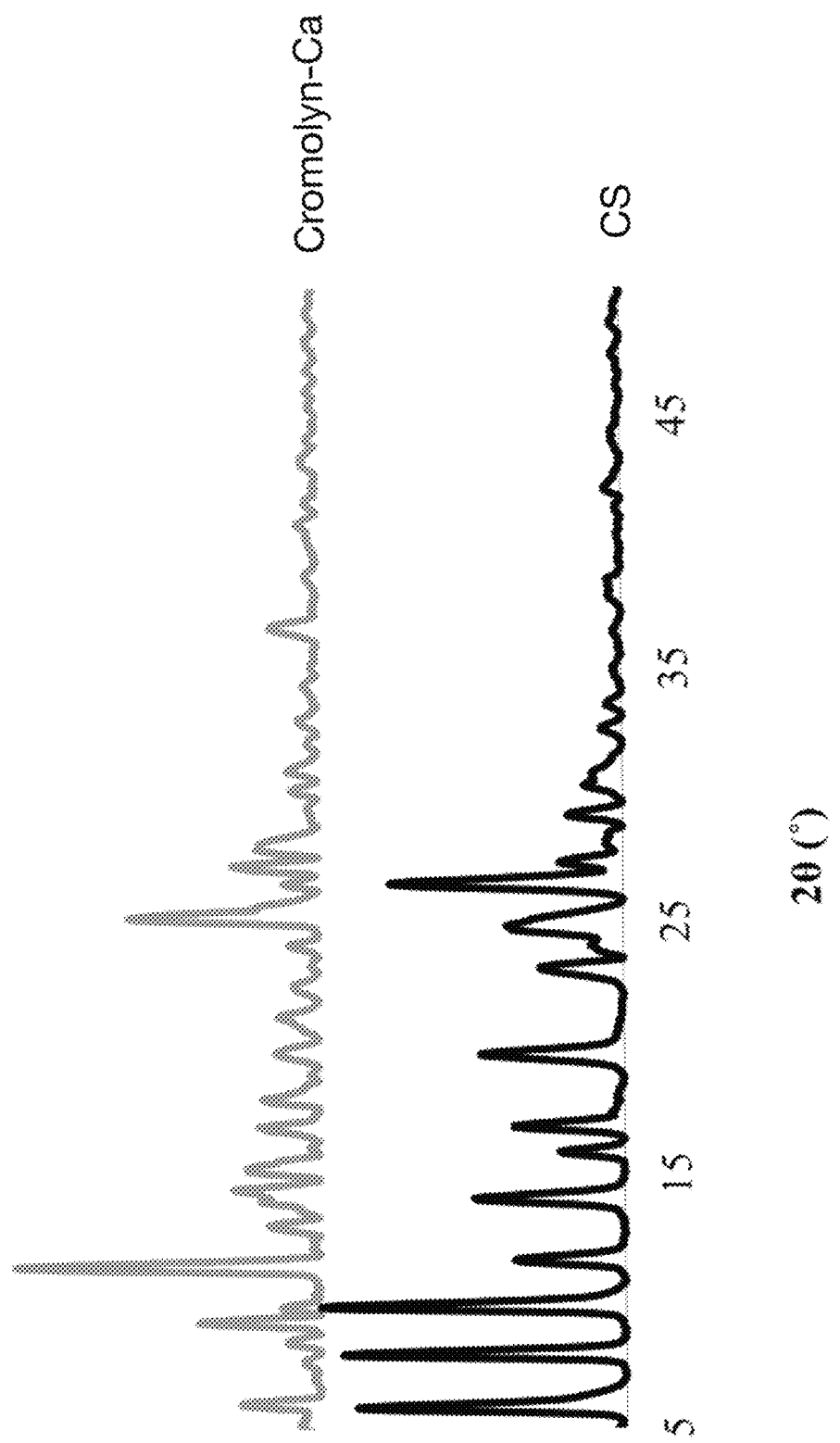
FIG. 15 illustrate the overlay of the experimental powder X-ray diffraction pattern of "as received" CS compared to synthesized Cromolyn-Ca.

Micro-powder X-ray Diffraction (PXRD) analysis—An overlay of the experimental PXRDs for the products formed from the synthesis between cromolyn and these three bioactive metal ions is shown in FIG. 12. The overlay of the experimental powder X-ray diffraction pattern of CS compared to the each of the pMCs are shown in FIGS. 13-15.

TABLE 1

Powder X-ray Diffraction (PXRD) prominent 2θ peaks of cromolyn-based pMCs

| Cromolyn-Zn | | Cromolyn-Mg | | Cromolyn-Ca | |
| --- | --- | --- | --- | --- | --- |
| 2θ peaks (°) | Intensity | 2θ peaks (°) | Intensity | 2θ peaks (°) | Intensity |
| 5.56 | 4156.64 | 5.42 | 2049 | 6.02 | 4031.69 |
| 9.08 | 2731.94 | 10.84 | 7494.93 | 9.24 | 5700.81 |
| 12.94 | 10000 | 14.22 | 3993.38 | 11.46 | 9289.31 |
| 13.44 | 4946.51 | 15.24 | 4389.15 | 13.13 | 1500 |
| 15.52 | 6120.84 | 17.84 | 3967.23 | 14.04 | 3472.78 |
| 17.62 | 3124.33 | 19.7 | 4919.73 | 14.36 | 4393.65 |
| 18.22 | 3452.03 | 24.3 | 10000 | 14.81 | 2236 |
| 25.42 | 4761.37 | 25.2 | 3070.5 | 15.56 | 2450 |
| 26.06 | 4493.89 | 26.28 | 5619.61 | 25.66 | 10000 |
| 27.96 | 5888.58 | 26.74 | 6915.96 | 27.28 | 4475.88 |
| 28.38 | 3034.23 | 27.2 | 7477.2 | 27.9 | 3624.65 |
| 28.64 | 3581.22 | 30.8 | 3160.7 | 28.28 | 6490.87 |

Single Crystal X-ray Diffraction (SCXRD) analysis—The syntheses of cromolyn with each of the bioactive metals (Zn$^{2+}$, Mg$^{2+}$ and Ca$^{2+}$) resulted in crystals with good quality for structural elucidation by SCXRD. Structure elucidation confirmed the formation of three new, unreported, crystalline materials namely, Cromolyn-Zn, Cromolyn-Mg, and Cromolyn-Ca. The crystal structures were collected at low temperature (100 K) and solved using direct methods. A summary of the crystallographic parameters is provided in Table 2 below.

TABLE 2

Crystallographic parameters for the structure refinements of the Cromolyn-based pharmaceutical-based metal complexes, (a) Cromolyn-Zn, (b) Cromolyn-Mg, and (c) Cromolyn-Ca.

| pMC | Cromolyn-Zn | Cromolyn-Mg | Cromolyn-Ca |
| --- | --- | --- | --- |
| Empirical formula | [Zn$_2$(C$_{46}$H$_{40}$O$_{28}$)]·7H$_2$O | [Mg(C$_{23}$H$_{24}$O$_{16}$)]·H$_2$O | [Ca$_2$(C$_{46}$H$_{48}$O$_{32}$)]·4H$_2$O |
| FW (g/mol) | 1297.63 | 598.75 | 1265.06 |
| Space group | C 2/c | P$\bar{1}$ | P 2$_1$/n |
| Temp. (K) | 100.00 (10) | 100.01 (10) | 100.01 (10) |
| λ (Å) | 1.54184 | 1.54184 | 1.54184 |
| a (Å) | 31.90641 (18) | 7.34210 (1) | 7.0293 (3) |
| b (Å) | 6.99799 (5) | 10.37410 (1) | 29.2917 (7) |
| c (Å) | 22.92769 (14) | 16.8517 (2) | 12.7862 (4) |
| α (°) | 90 | 100.8990 (1) | 90 |
| β (°) | 95.6148 (6) | 98.9160 (1) | 99.495 (3) |
| γ (°) | 90 | 93.5560 (1) | 90 |
| V (Å$^3$) | 5094.75 (5) | 1239.64 (3) | 2596.61 (15) |
| Z | 4 | 2 | 2 |
| ρ$_{calc}$ (g/cm$^3$) | 1.692 | 1.604 | 1.618 |
| R$_{wp}$ | 0.0790 (4714) | 0.1246 (4543) | 0.1997 (4797) |
| R$_p$ | 0.0304 (4429) | 0.0455 (4196) | 0.0792 (4282) |

These results confirmed that the reaction precipitate was not produced by the simple recrystallization of the metal salt or the ligand. The low amorphous background observed in the powder diffractograms for the isolated phases indicate a high degree of crystallinity in these materials. The appearance of different reflections when compared to one another and CS suggests that distinct phases were produced under these reaction conditions. The absence of low angle peaks (<5° in 2θ) in the diffractogram indicates that these materials are most likely dense structures having 2D layers, as opposed to 3D porous networks. This result suggests that the molecular structure of CS might not permit flexible 3D structures to form.

Figure 16:
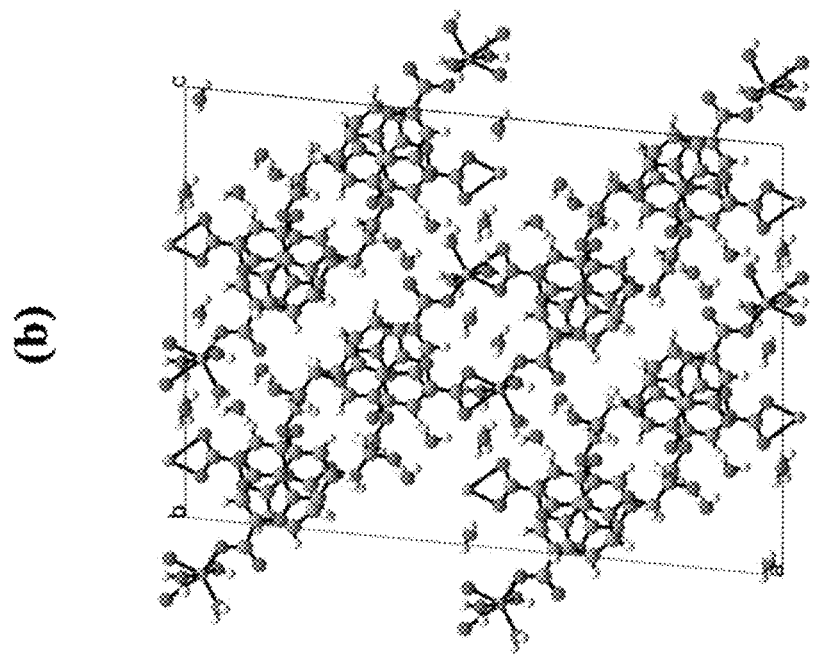
FIG. 16 illustrate the molecular structure of (a) the asymmetric unit, and (b) crystalline packing of Cromolyn-Zn along b-axis.
Figure 16:
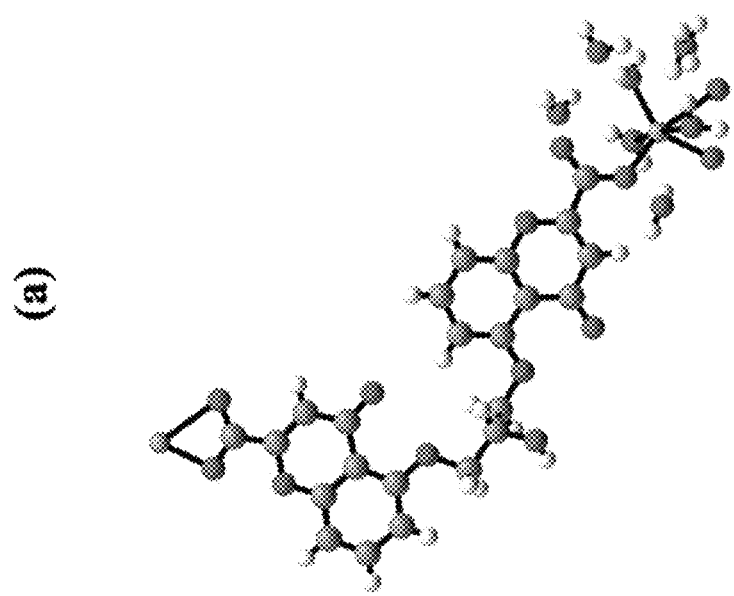
Figure 17:
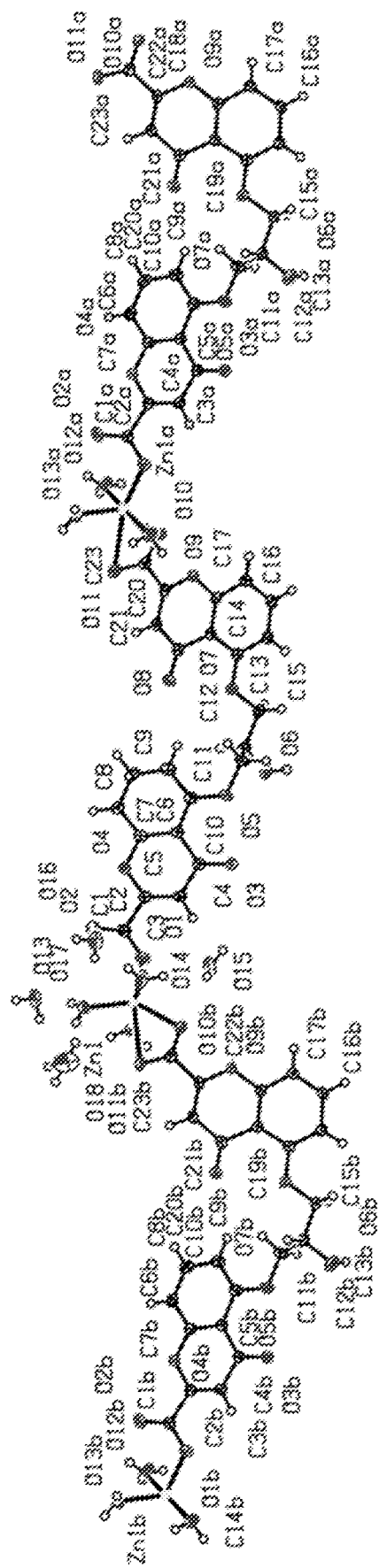
FIG. 17 shows an ORTEP (atoms labeled) representation of Cromolyn-Zn.
Figure 18:
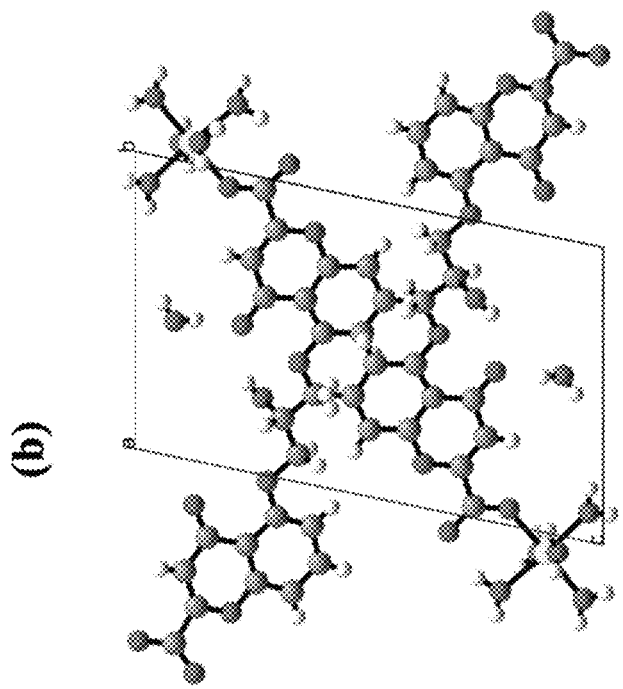
FIG. 18 illustrate the molecular structure of (a) the asymmetric unit, and (b) crystalline packing of Cromolyn-Mg along a-axis.
Figure 18:
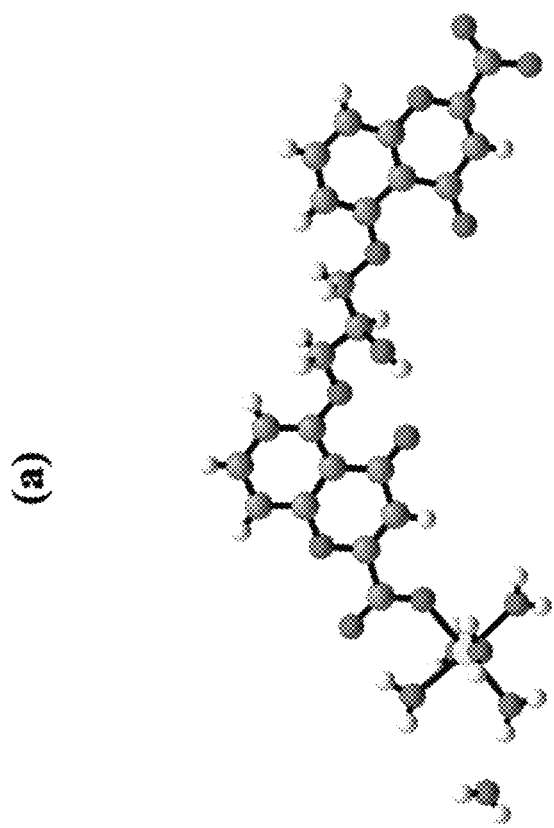
Figure 19:
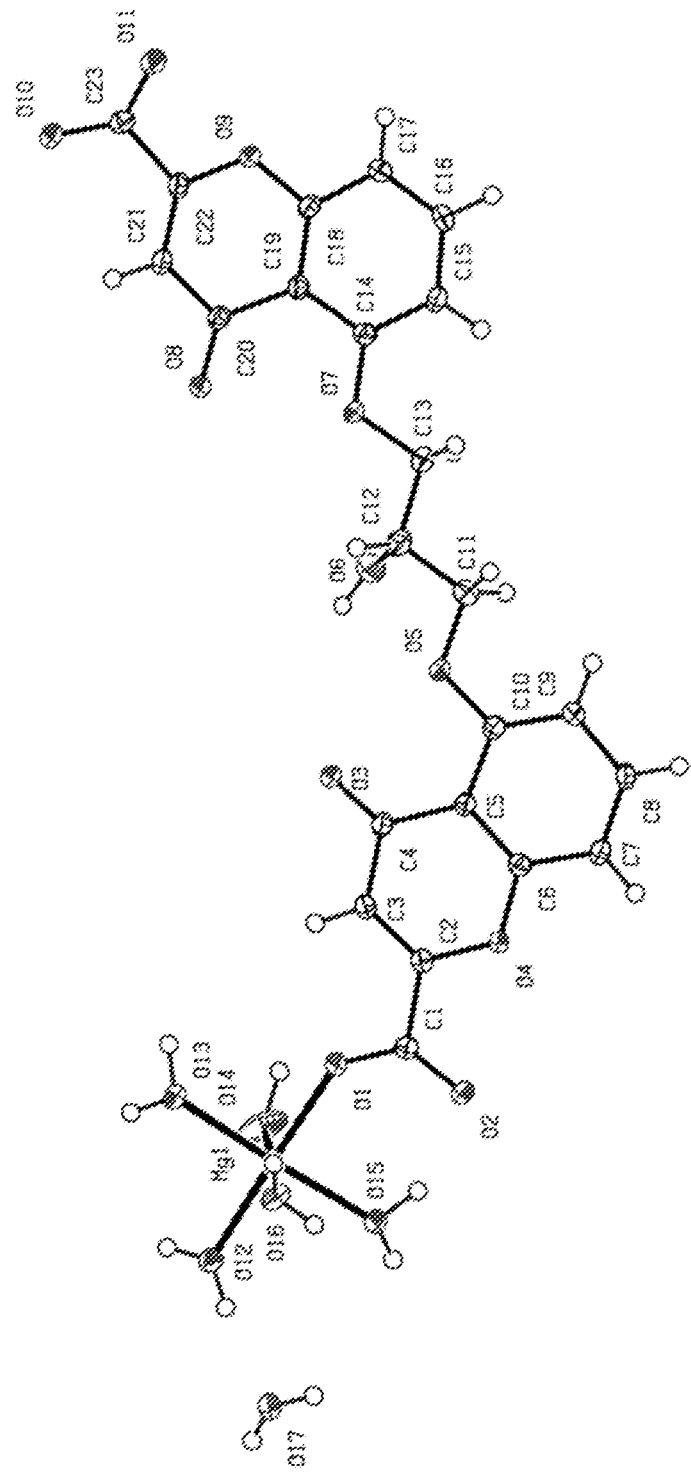
FIG. 19 shows an ORTEP (atoms labeled) representation of Cromolyn-Mg.
Figure 20:
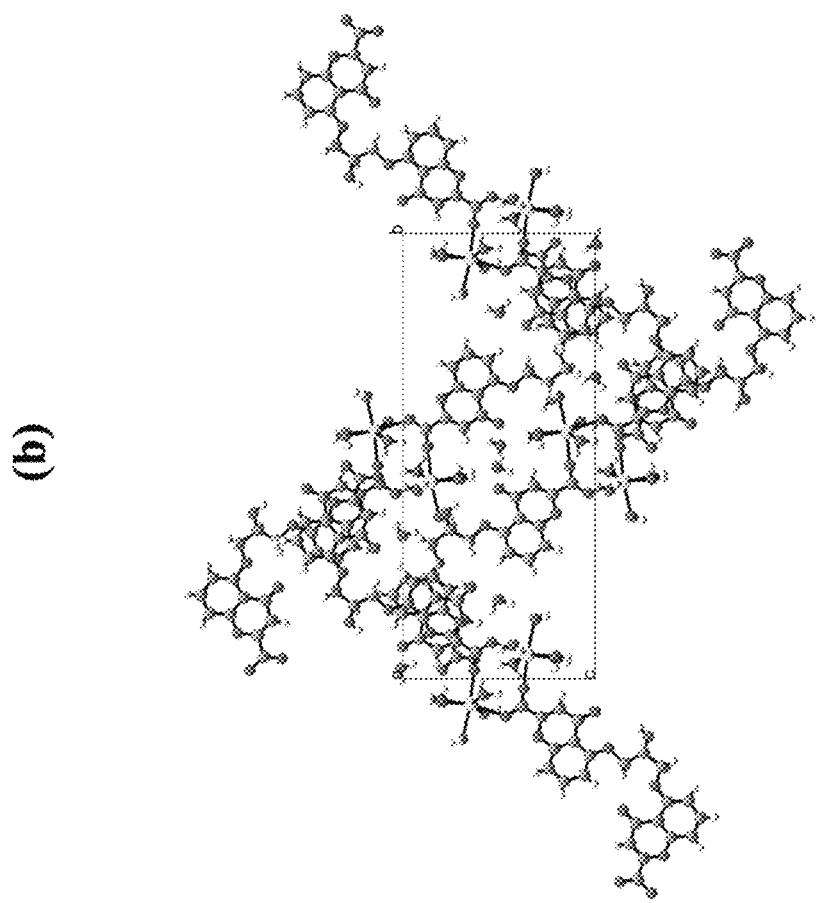
FIG. 20 illustrate the molecular structure of (a) the asymmetric unit, and (b) crystalline packing of Cromolyn-Ca along a-axis.
Figure 20:
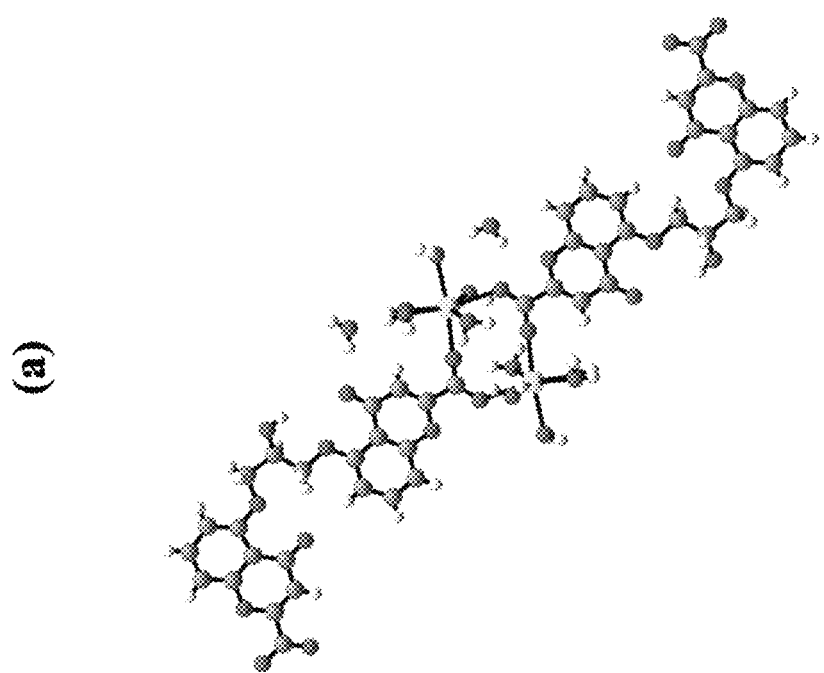
Figure 21:
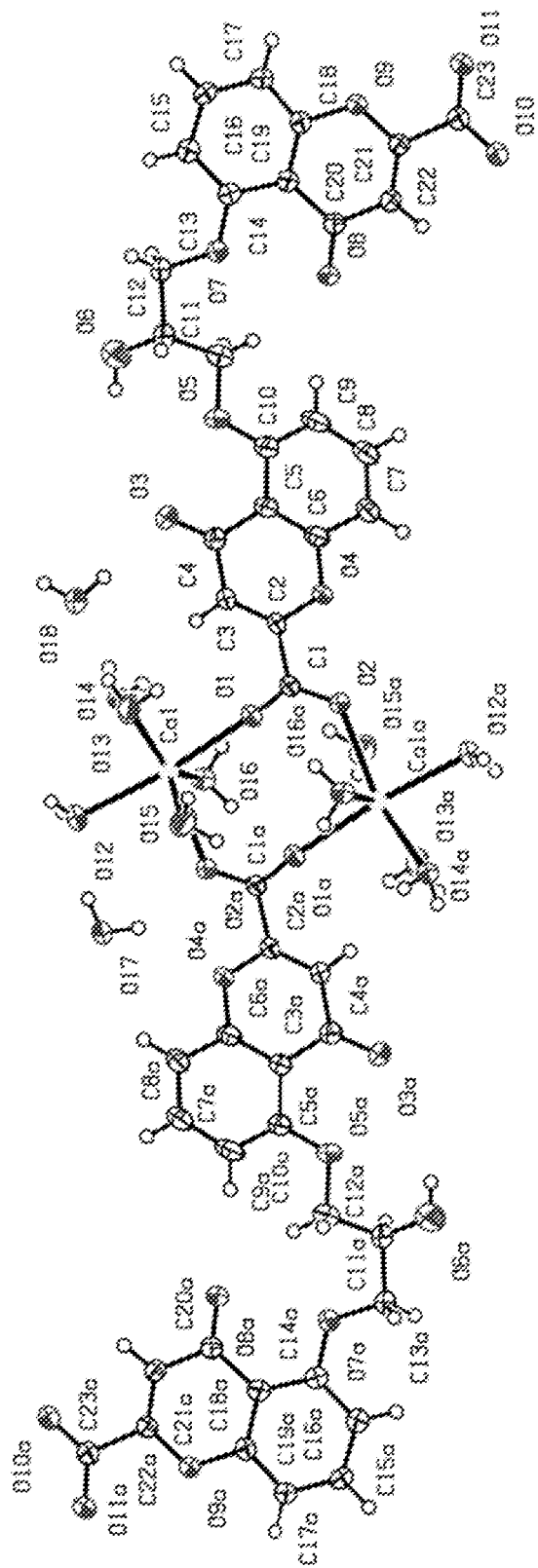
FIG. 21 shows an ORTEP (atoms labeled) representation of Cromolyn-Ca.
Figure 22:
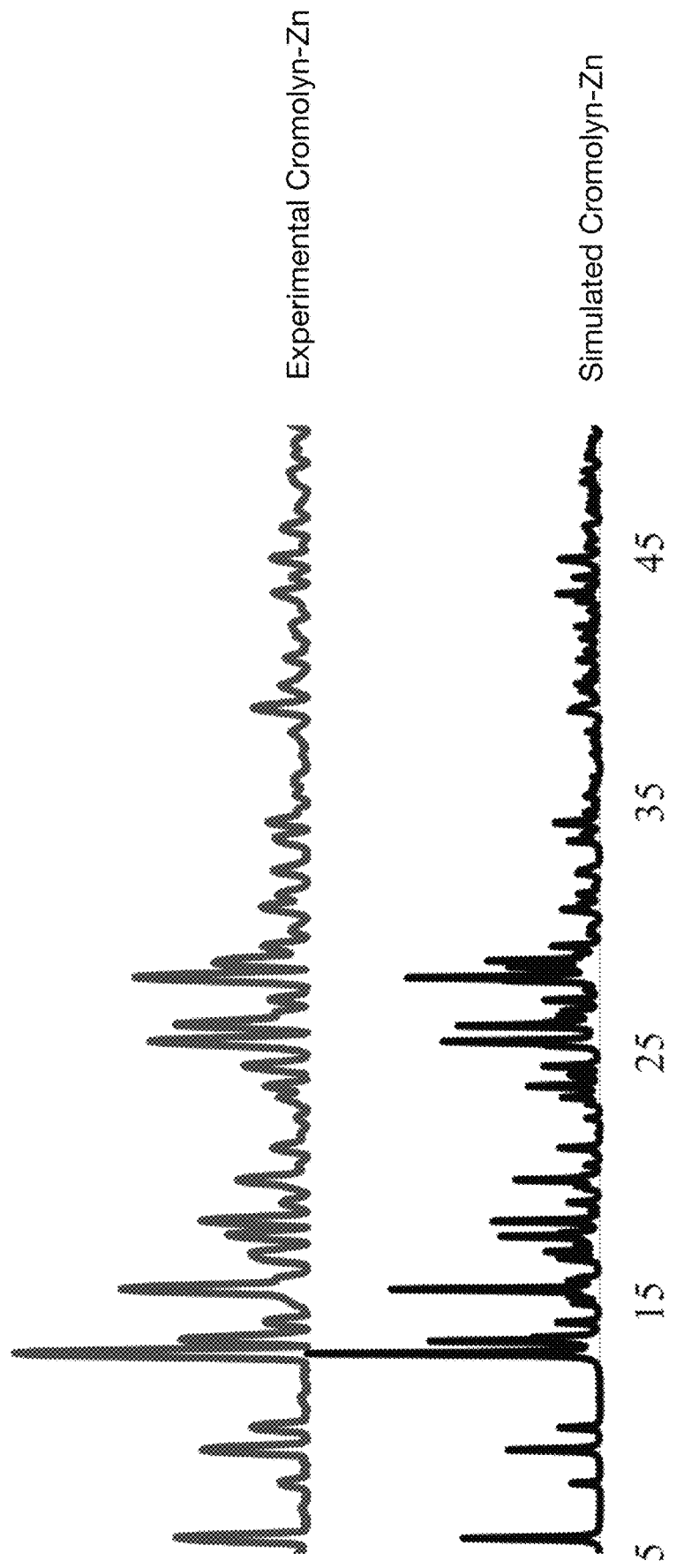
FIG. 22 shows simulated and experimental powder X-ray diffraction pattern overlay of Cromolyn-Zn carried out at 100 K.
Figure 23:
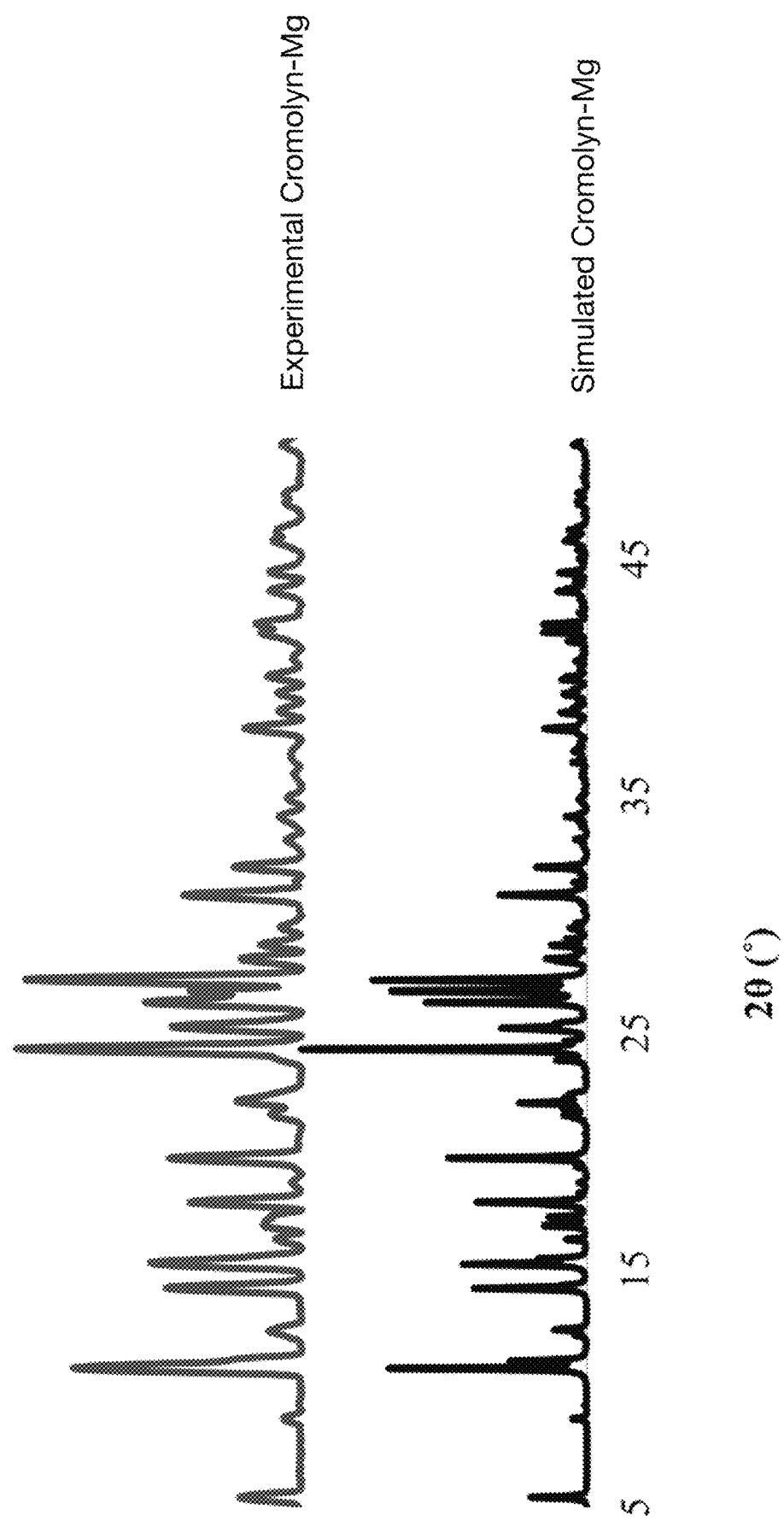
FIG. 23 shows simulated and experimental powder X-ray diffraction pattern overlay of Cromolyn-Mg carried out at 100 K.
Figure 24:
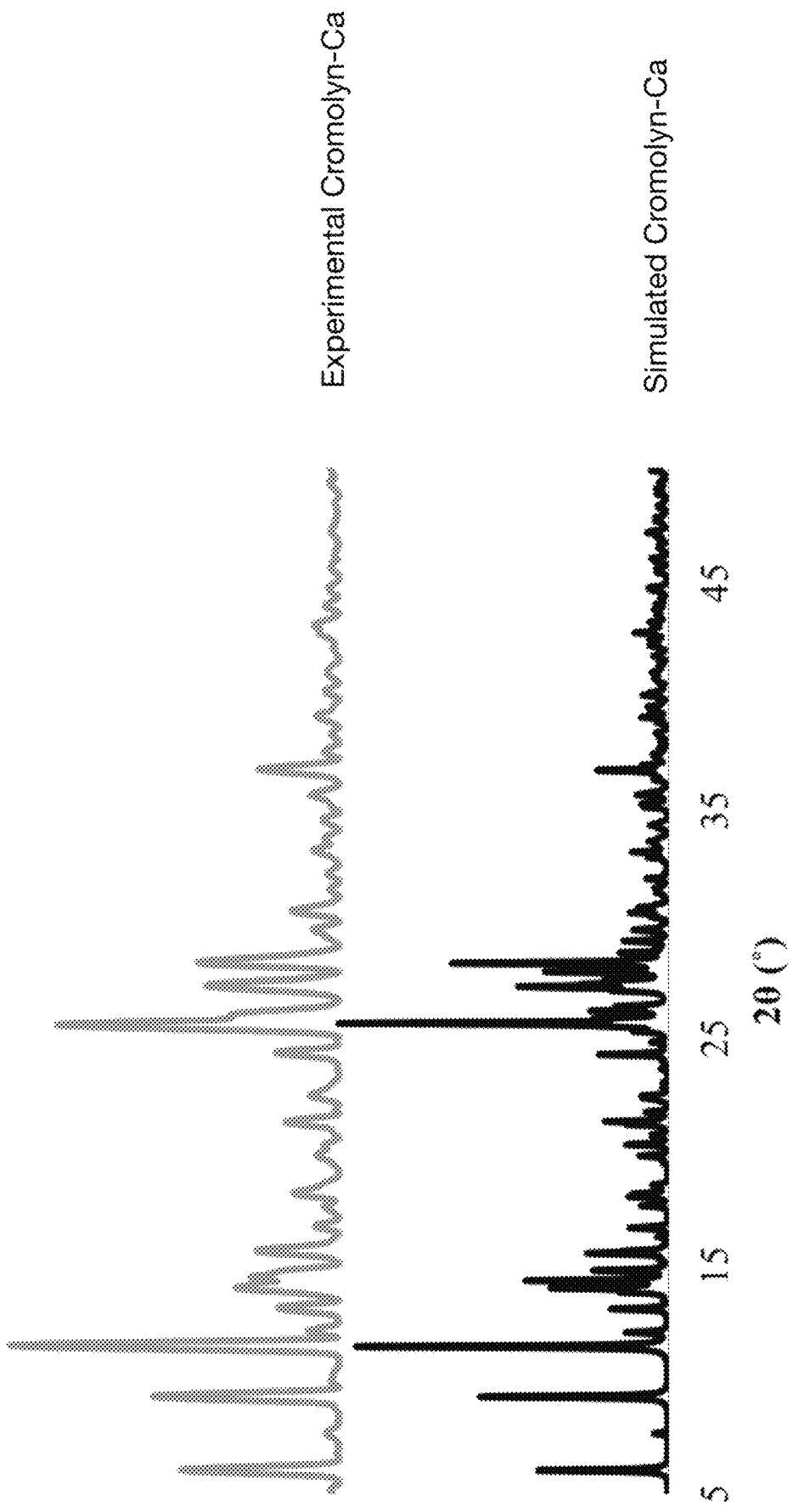
FIG. 24 shows simulated and experimental powder X-ray diffraction pattern overlay of Cromolyn-Ca carried out at 100 K.

FIGS. 16, 18, and 20 illustrate the molecular structure, and asymmetric unit of Cromolyn-based pMCs. FIGS. 17, 19, and 21 presents the ORTEPs for the refined structures of the Cromolyn-based pMCs. FIGS. 22-24 portray overlay of the simulated and experimental powder patterns for the structures solved within this study. These results indicate a proper solution has been produced for each of the bulk phases represented in these pMCs.

Structural description of Cromolyn-Zn—The compound [Zn$_2$(C$_{46}$H$_{40}$O$_{28}$)]·7H$_2$O crystallizes in the monoclinic space group C2/c with half a molecule in the asymmetric unit. The structure presents a distorted octahedral with three metal oxygen bonds (Zn1-O12=2.084 Å, Zn1-O13=1.973 Å, and Zn1-O14=2.197 Å) formed by coordinated water molecules and other three metal oxygen bonds (Zn1-O1=1.973 Å, Zn1-O10=2.041 Å, and Zn1-O11=1.973 Å) coordinated to the ligand. Intermolecular hydrogen bonds reinforce the conformation of the ligand (O7-O8=2.670 Å and O3-O5=2.653 Å), while an intricate network of intermolecular hydrogen bonds propagates the packing of this metal complex along the a-c plane. Over ten unique hydrogen bonds (O12-O15=2.798 Å, O12-O16=2.698 Å, O13-O17=2.681 Å, O14-O18=2.936 Å, O17-O18=2.919 Å, O1-O15=3.017 Å, O10-O15=2.967 Å, O3-O17=2.780 Å, O5-O17=2.937 Å, and O11-O13=2.721 Å) are formed hinting at the importance contribution of the four lattice water molecules present in this crystal structure to the formation of this packing motifs.

Structural description of Cromolyn-Mg—The compound [Mg($C_{23}H_{24}O_{16}$)]·$H_2O$ crystalized in the triclinic space group $P\overline{1}$ and has one molecule in the asymmetric unit. In the structure cromolyn acts as a monodentate ligand coordinated to one magnesium atom through a metal oxygen bond (Mg1-O1=2.037 Å) in the equatorial position. Five water molecules (two axial and 3 equatorial) are coordinated to the metal center and complete a nearly perfect octahedra. The metal cluster demonstrates a highly conserved octahedral geometry with the O—Mg—O bond angles ranging from 87.45 to 95.26°. The conformation of the asymmetric unit is reinforced by strong intramolecular hydrogen bonds (O3-O5=2.684 Å, O7-O8=2.697 Å, and O2-O15=2.748 Å). The asymmetric unit expands tilted along the b-axis (O8-O12=2.804 Å, O3-O15=2.786 Å, O10-O17=2.876 Å, and O12-O17=2.716 Å) and the a-axis (O6-O16=2.840 Å and O8-O16=2.738 Å) through additional hydrogen bonds. Many of these hydrogen bonds are enabled by the presence of the only lattice water present in this crystal structure.

Structural description of Cromolyn-Ca—The compound [$Ca_2$($C_{46}H_{48}O_{32}$)]·$4H_2O$ crystallizes in the monoclinic space group $P2_1/n$ and has one molecule in the asymmetric unit. In the structure, cromolyn acts as a bridging ligand coordinated to calcium atoms through metal oxygen bonds in both the axial position (Ca1-O1=2.327 Å) and equatorial position (Ca1-O2=2.460 Å) forming distorted pentagonal bipyramid geometry with five coordinated water molecules. The Ca—O bond distances for the water molecules range between 2.394 and 2.460 Å. The O—Ca—O bond angles range from 67.58 to 100.06°. Two lattice water molecules are present in the structure. The conformation is reinforced by both inter- and intramolecular bonds. Intramolecular bonds occur mainly with the lattice water molecules (O3-O5=2.670 Å, O1-O16=3.007 Å, and O7-O8=2.667 Å). This motif propagates along the a-axis (O15-O16=2.996 Å) through hydrogen bonds. Various hydrogen bonds also help expand this motif along the b-c plane (O15-O10=2.859 Å, O10-O16=2.666 Å, and O11-O14=2.844 Å).

Figure 25:
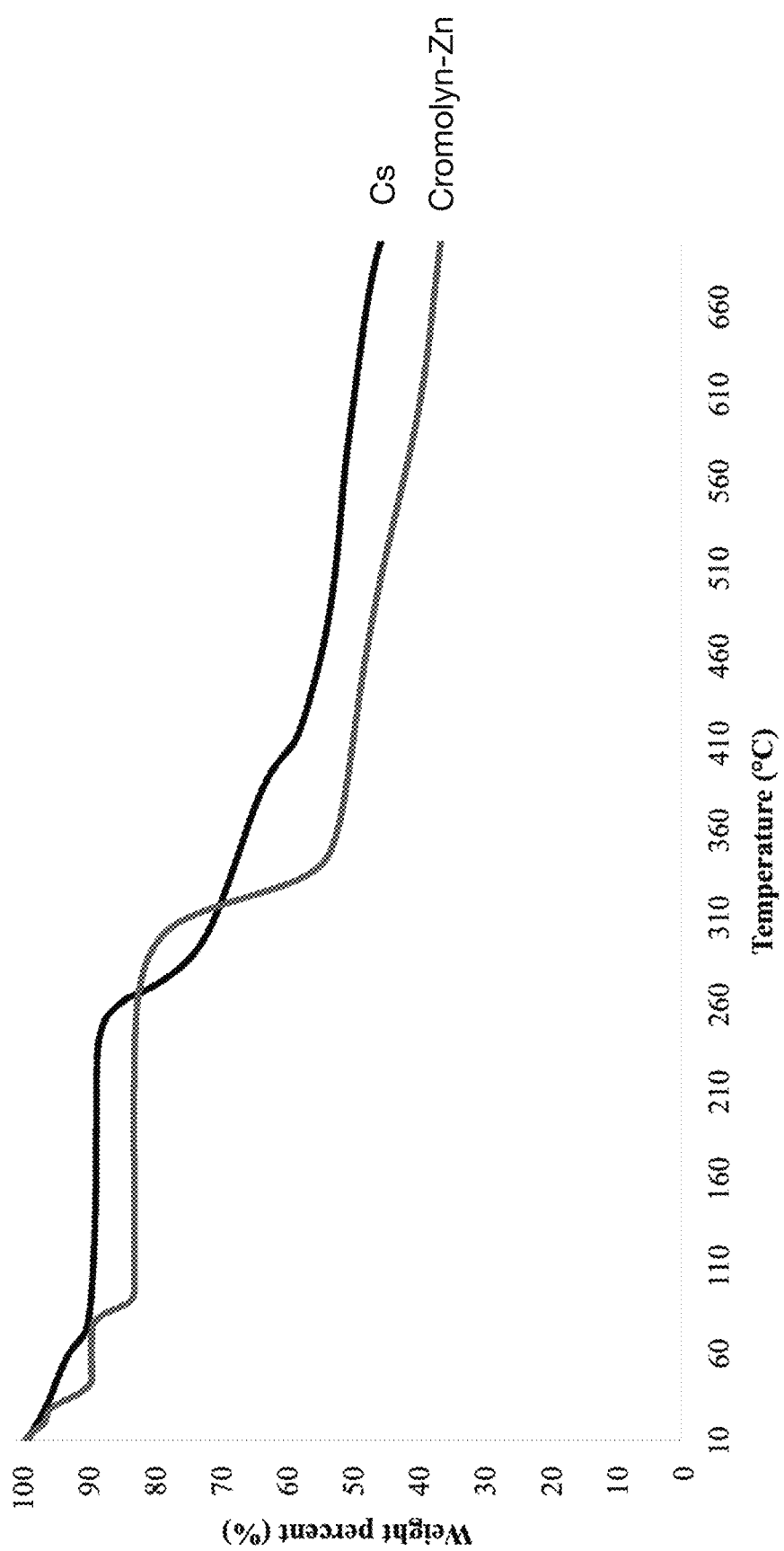
FIG. 25 depicts the overlay of the TGA thermograph for Cromolyn-Zn with CS.
Figure 26:
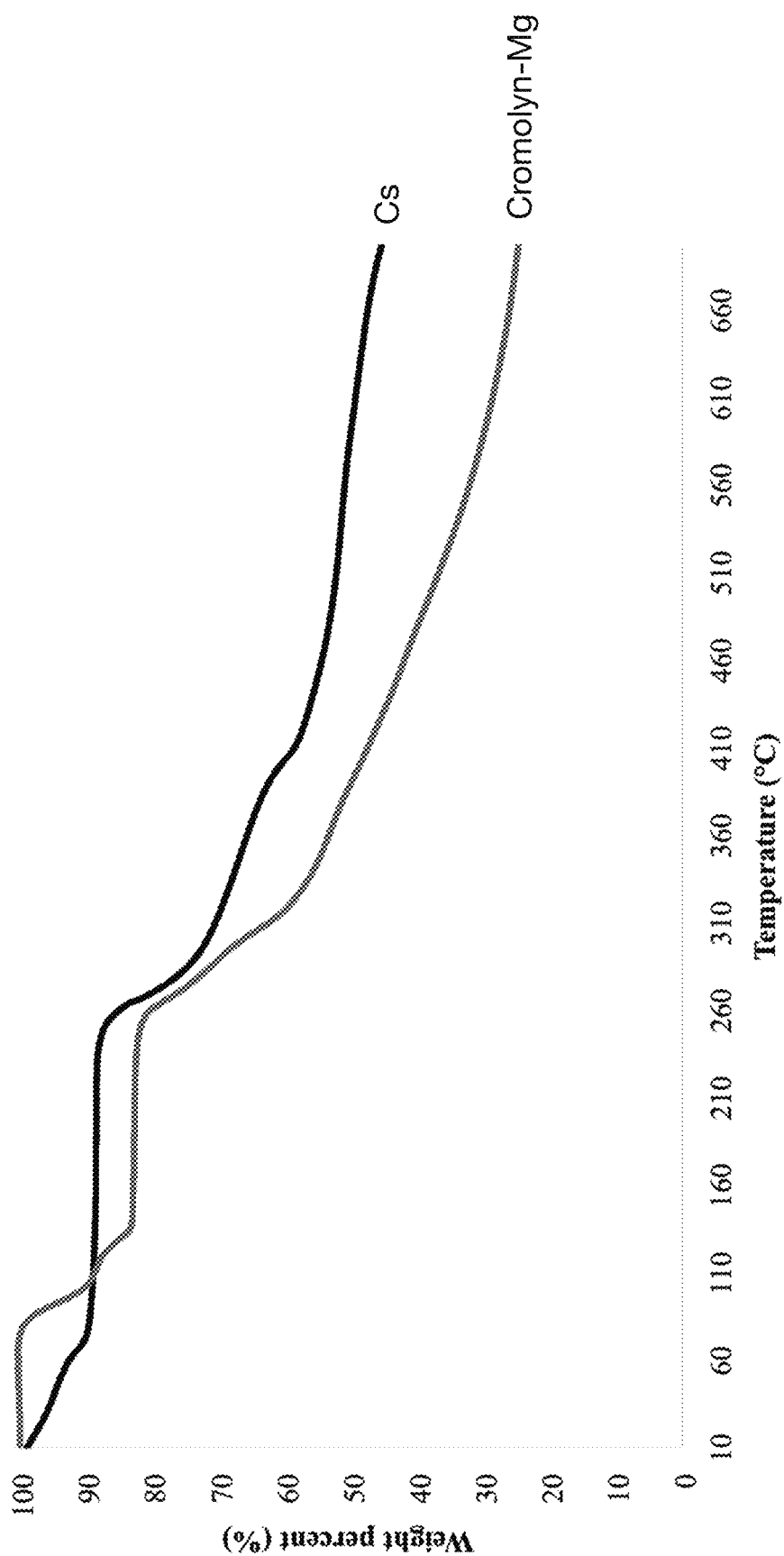
FIG. 26 depicts the overlay of the TGA thermograph for Cromolyn-Mg with CS.
Figure 27:
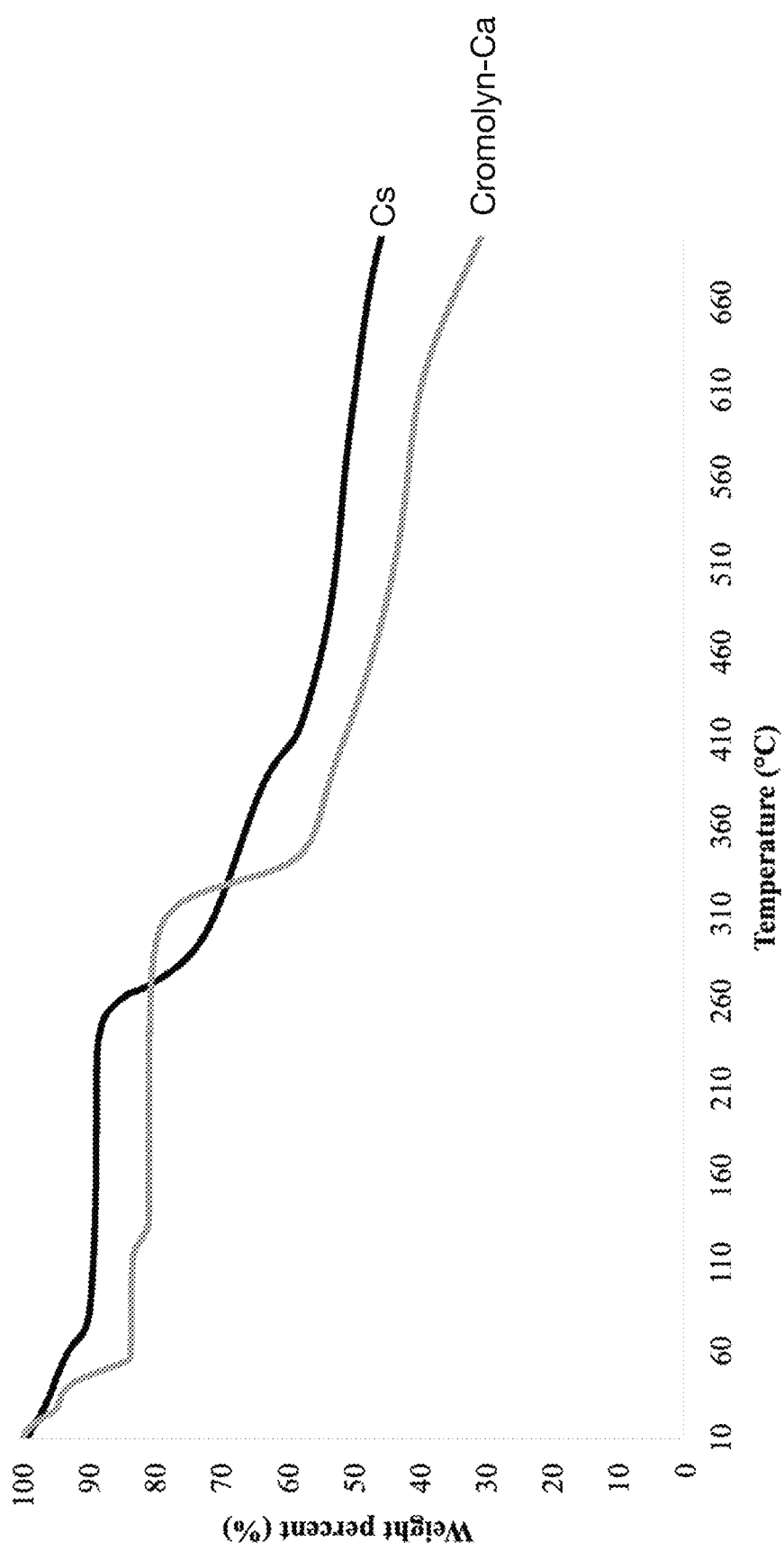
FIG. 27 depicts the overlay of the TGA thermograph for Cromolyn-Ca with CS.

Thermogravimetric Analysis (TGA) results—TGA was employed to measure the decomposition of these materials as a function of temperature (FIGS. 25-27). It was expected that the thermograph of each metal complex consists of at least three decomposition events. The first event occurs at a lower temperature and corresponds to the removal of coordinated and guest water molecules. The second and the final decomposition events observed correspond to the thermal degradation of the metal complex and metal/metal oxide, respectively. As observed in FIGS. 25-27, all three pMCs present unique thermographs.

The TGA thermograph of Cromolyn-Zn (FIG. 25) starts with a low temperature (30-130° C.) weight loss of 17.2 wt. % (Calculated=18.0 wt. %), most likely due to the loss of coordinated and lattice water molecules present in this metal complex, afterwards a second thermal event presents a weight loss of 31.70 wt. % occurring around 250-360° C. This corresponds to the decomposition of Cromolyn-Zn. Subsequently, a higher temperature (360-700° C.) weight loss of 15.33 wt. % occurred, which was attributed to the degradation of zinc/zinc oxide.

The TGA thermograph of Cromolyn-Mg (FIG. 26) starts with a low temperature (30-130° C.) loss of 17.0 wt. % (Calculated=18.0 wt. %), that occurs as a consequence of the loss of the coordinated and lattice water molecules present in this metal complex.

Afterwards a second thermal event (230-360° C.) is shown with a weight loss of 29.62 wt. %. This degradation is attributed to the decomposition of Cromolyn-Mg. Subsequently, between 360-700° C. a weight loss of 28.70 wt. % occurred due to the degradation of magnesium/magnesium oxide.

The TGA thermograph of Cromolyn-Ca (FIG. 27) starts with a low temperature (30-130° C.) weight loss of 19.4 wt. % (Calculated=19.9 wt. %). This is most likely a consequence of the loss of coordinated and lattice water molecules present in this metal complex. Subsequently, a second thermal event occurs at a higher temperature range (250-360° C.), which accounts for a weight loss of loss of 29.78 wt. %. The second thermal event is attributed to the decomposition of Cromolyn-Ca. A third degradation with a weight loss of 34.25 wt. % occurs between 360 and 700° C. and is attributed to the degradation of calcium/calcium oxide.

The differences in the thermal behavior of CS and the pMCs observed between 10-140° C. is most likely due to the loss of coordinated and lattice water molecules present in each Cromolyn-based pMCs. The second event occurs at a temperature range between 230 and 360° C. and corresponds to the decomposition of the metal complex. A greater percent weight loss in this temperature range is observed in the thermographs of the pMCs compared to that of CS. The degradation of the metal/metal oxide takes place at a higher temperature range (360-700° C.). These pMCs show a higher thermal stability when compared to CS, the pMCs present a higher weight loss (>330° C.) when coordinated.

Dissolution Profile

Stock Solution: A standard stock solution of CS was prepared by dissolving 10 mg in a 100 mL (0.1 mg/mL) volumetric flask and completing to volume with PBS. Dilute solutions were obtained by appropriate dilution of this stock solution.

Figure 28:
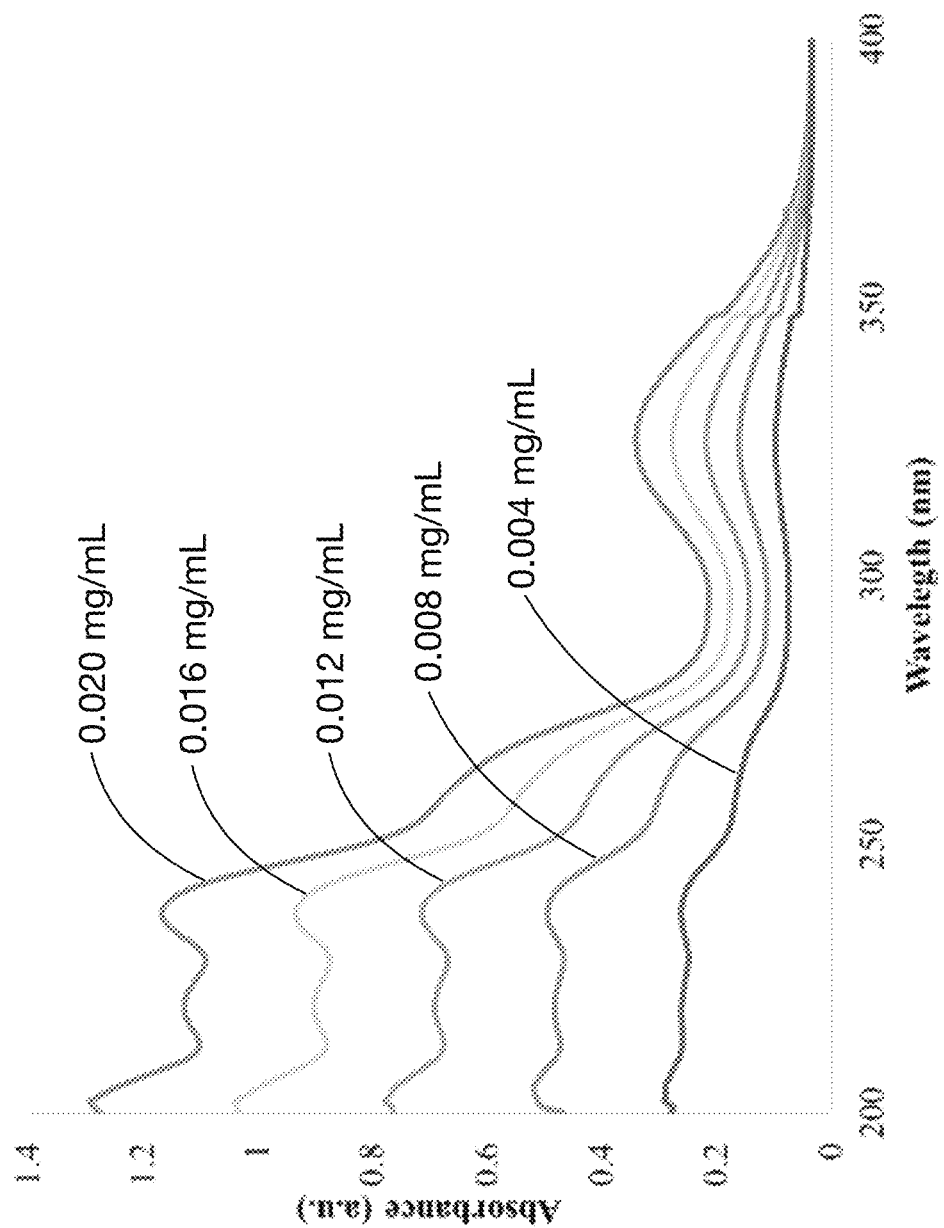
FIG. 28 shows Absorbance spectra of CS presenting a maximum absorption wavelength ($\lambda_{max}$) at 237 nm in PBS.
Figure 29:
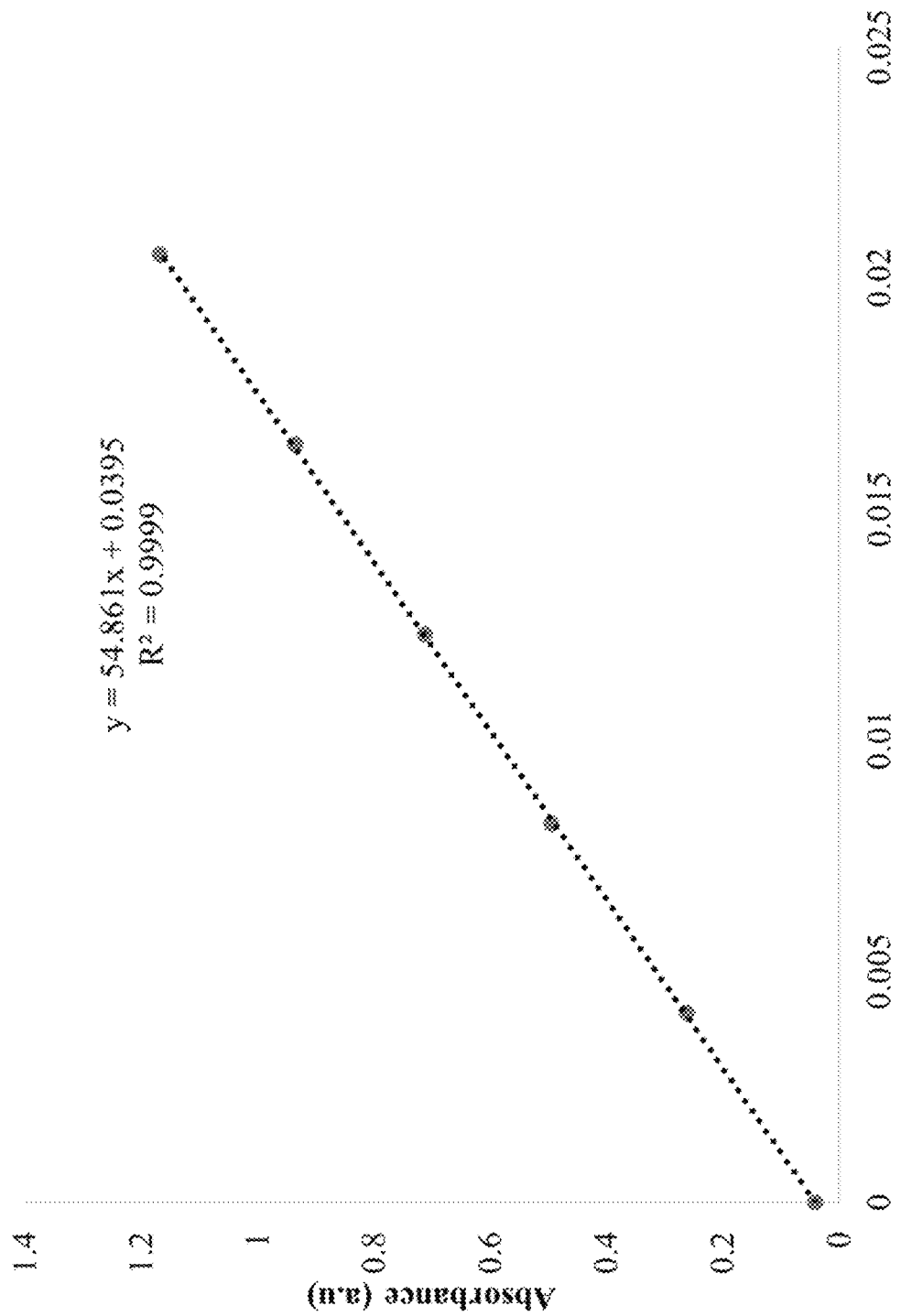
FIG. 29 shows the calibration curve of CS in PBS (0.004-0.02 mg/mL).

Calibration Curve: Accurately measured aliquots of the stock solution were transferred into a series of volumetric flasks and resulted in standard solutions with a concentration range between 0.004 and 0.02 mg/mL. PBS was used as the solvent. The absorbance of CS was measured at maximum absorption wavelength ($\lambda_{max}$) of 237 nm against a solvent blank (PBS). FIG. 28 displays the absorbance spectra of CS presenting a maximum absorption wavelength (Amax) at 237 nm in PBS. At $\lambda$=237 nm, the metal complexes do not absorb, and thus, only the excitation spectrum of CS would be recorded. FIG. 29 presents the calibration curve of CS in PBS.

The stability of these materials in biologically relevant media was used to understand the ability of the pMCs to sustain blood plasma concentration for CS. A higher blood concentration might allow for longer circulation times and adequate delivery to the target tissues and organs. This is currently a pharmacological disadvantage for oral formulations of CS (<1% bioavailability and low solubility ~100.0 mg/mL at 20° C.). The dissolution of these materials was first studied in FaSSGF (pH=1.60) where it was observed that CS and the pMCs did not degrade significantly (no detectable dissolution) at 37° C. Therefore, no further dissolution studies were carried out in this media.

Dissolution profiles were recorded for CS, Cromolyn-Zn, Cromolyn-Mg, and Cromolyn-Ca. Dissolution assays were performed for CS—Zn and CS—Ca in 150 mL of PBS buffer (pH=7.40), controlling the temperature at 37° C. and stirring at 150 rpm. About 30 mg of pulverized Cromolyn-Zn and Cromolyn-Ca was used for the dissolution measurements. In the case of Cromolyn-Mg, ~10 mg of the pulverized solid was employed for the dissolution profile measurement and the total volume of PBS in the dissolution vessel was decreased to 100 mL.

Figure 30:
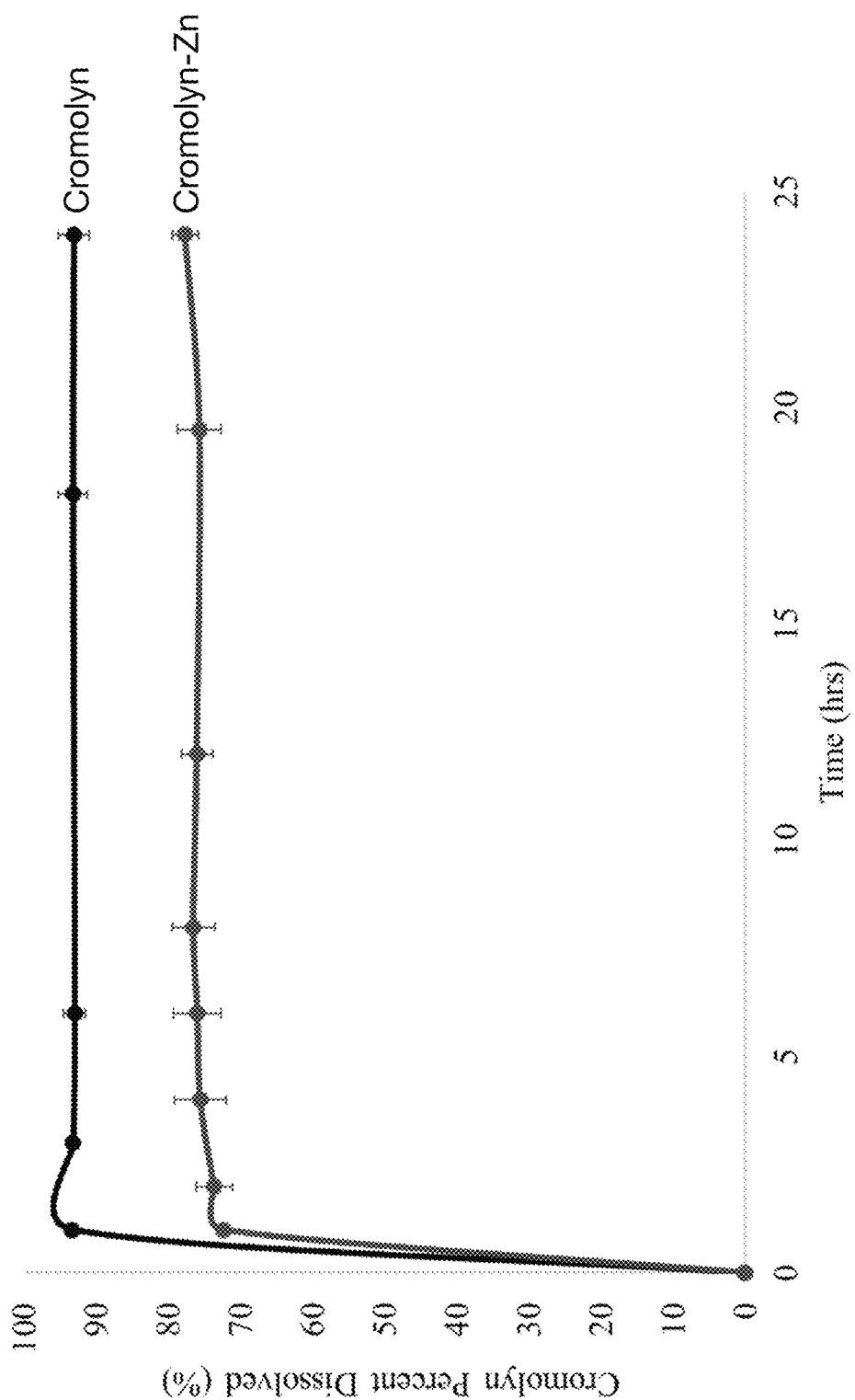
FIG. 30 shows the dissolution profile (24 hrs.) in PBS of CS and Cromolyn-Zn.
Figure 31:
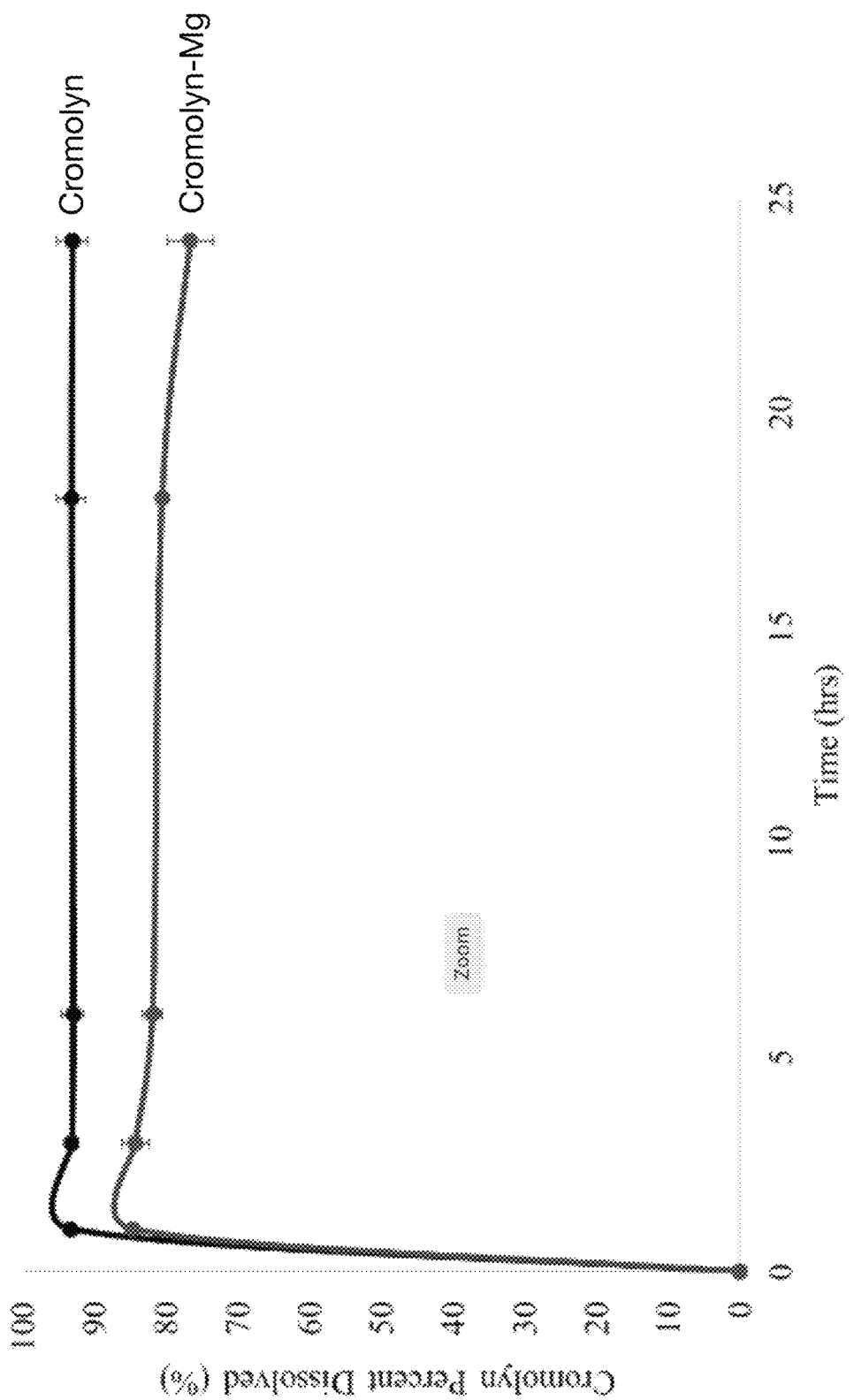
FIG. 31 shows the dissolution profile (24 hrs.) in PBS of CS and Cromolyn-Mg.
Figure 32:
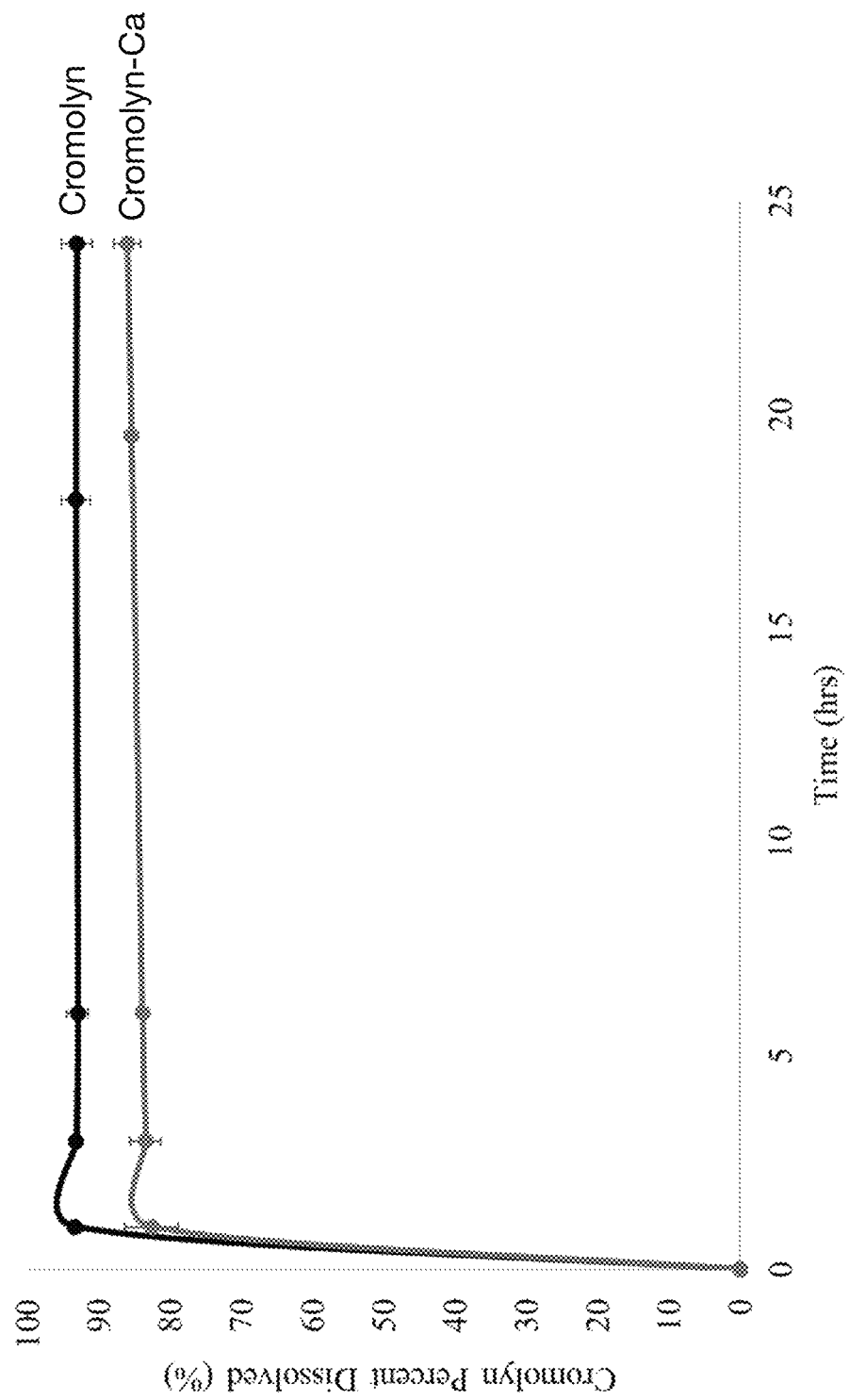
FIG. 32 shows the dissolution profile (24 hrs.) in PBS of CS and Cromolyn-Ca.

The pulverized powder of each CS metal complex was added to the respective volume of PBS at the beginning of the dissolution while the temperature (37° C.) and stirring was constant (150 rpm). Aliquots of 1 mL were collected at 0, 1, 2, 4, 6, 8, 12, 19.5 and 24 hrs. for Cromolyn-Zn, for Cromolyn-Mg aliquots were collected at 0, 1, 3, 6, 19.5, and 24 hrs., and for Cromolyn-Ca aliquots were collected at 0, 1, 3, 6, 18, and 24 hrs. The aliquots were placed in 10 mL volumetric flasks and completed to volume with PBS. The absorbance of CS was measured at 237 nm against the solvent blank. The comparison of the dissolution profiles of each metal complex against CS is displayed on FIGS. 30-32. Absorbance measurements were performed on an Agilent Technologies Cary Series UV-Vis Spectrophotometer, Cary 100 UV-Vis; using the UV Cary Scan software version v.20.0.470. All measurements were performed with a 400-200 nm scan.

As previously explained, PBS (pH=7.40) was used as media to determine the dissolution profiles of these materials relative to CS. The absorbance was measured at the maximum wavelength ($\lambda_{max}$=237 nm) for CS as the degradation of the pMCs progressed in PBS over time. The dissolution profiles showed a slow release of CS from the pMCs, which reached its maximum concentration (~98%) after 1 hr. The rate at which CS was released varied among the pMCs. These results conclude that Cromolyn-Zn (~75% in 5 hrs.), Cromolyn-Mg (~80% in 6 hrs.), and Cromolyn-Ca (~85% in 6 hrs.) possess a high stability and degrade slowly over time. The concentration at which the metal complex reached equilibrium in PBS at 37° C. was calculated as 0.17 mg/mL for Cromolyn-Zn and Cromolyn-Ca, and 0.10 mg/mL for Cromolyn-Mg. Results indicate that these materials could circulate for a longer time and potentially reach the target site under physiological conditions. CIF files have been deposited in the Cambridge Crystallographic Data Centre (CCDC) Depository, CCDC 2013974-2013976.

CONCLUSIONS

The coordination of this therapeutic mast cell stabilizer with bioactive metals ($Zn^{2+}$, $Mg^{2+}$ and $Ca^{2+}$) produced three distinct Cromolyn-based pMCs, namely, Cromolyn-Zn, Cromolyn-Mg, and Cromolyn-Ca. The conditions that led to the successful syntheses of these materials and their solid-state was characterized using Raman spectroscopy, PXRD, SEM-EDS, TGA and SCXRD. These results confirm the composition, thermal stability, and packing modes of these crystalline materials. None of these conditions resulted in 3D flexible structures. To the best of the inventors' knowledge, no other metal complexes employing CS have been reported in the literature; therefore, these represent the first three of such materials.

Although only 2D structures were observed under the conditions studied, the unique binding modes and packing motifs present in these materials might affect the activity and delivery of CS. Dissolution studies provided a grasp on the structural stability in PBS. Dissolution occurred slowly suggesting a higher degree of structural stability (slow degradation) under neutral physiological conditions while in acidic conditions no significant degradation of the Cromolyn-based pMCs occurred. Further exploration of the conditions needed to form 3D flexible Cromolyn-based pMCs could lead to the development of novel multi-drug delivery systems to better mitigate allergic and inflammatory diseases.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. A pharmaceutical metal complex (pMC) comprising: a metal coordination complex of cromolyn coordinated with a metal selected from the group consisting of: $Ca^{2+}$, $Zn^{2+}$, and $Mg^{2+}$.

2. The pMC according to claim 1, wherein said metal coordination complex has a single crystal form characterized by major x-ray powder diffraction peaks at 2Θ angles of 6.02, 9.24, 11.46, 13.13, 14.04, 14.36, 14.81, 15.56, 25.66, 27.28, 27.9, and 28.28 when said metal is $Ca^{2+}$.

3. The pMC according to claim 1, wherein said metal coordination complex has a single crystal form characterized by major x-ray powder diffraction peaks at 2Θ angles of 5.56, 9.08, 12.94, 13.44, 15.52, 17.62, 18.22, 25.42, 26.06, 27.96, 28.38, and 28.64 when said metal is $Zn^{2+}$.

4. The pMC according to claim 1, wherein said metal coordination complex has a single crystal form characterized by major x-ray powder diffraction peaks at 2Θ angles of 5.42, 10.84, 14.22, 15.24, 17.84, 19.7, 24.3, 25.2, 26.28, 26.74, 27.2, and 30.8 when said metal is $Mg^{2+}$.

5. The pMC of claim 2, wherein the single crystal form is characterized by the X-ray powder diffraction pattern of FIG. 24.

6. The pMC of claim 3, wherein the single crystal form is characterized by the X-ray powder diffraction pattern of FIG. 22.

7. The pMC of claim 4, wherein the single crystal form is characterized by the X-ray powder diffraction pattern of FIG. 23.

8. The pMC of claim 2, wherein the single crystal form has a monoclinic unit cell with cell parameters: a=7.0293(3) Å, b=29.2917(7) Å, c=12.7862(4) Å and β=99.495(3)°.

9. The pMC of claim 3, wherein the single crystal form has a monoclinic unit cell with cell parameters: a=31.90641 (18) Å, b=6.99799(5) Å, c=22.92769(14) Å and β=95.6148 (6)°.

10. The pMC of claim 4, wherein the single crystal form has a triclinic unit cell with cell parameters: a=7.34210(1) Å, b=10.37410(1) Å, c=16.8517(2) Å and β=98.9160 (1)°.

11. The pMC of claim 2, wherein the single crystal form has monoclinic space group of P 21/n.

12. The pMC of claim 3, wherein the single crystal form has monoclinic space group of C 2/c.

13. The pMC of claim 4, wherein the single crystal form has triclinic space group of P$\bar{1}$.

* * * * *